United States Patent
Tsai et al.

(10) Patent No.: US 7,365,239 B2
(45) Date of Patent: Apr. 29, 2008

(54) IN VIVO MODELS FOR RABGEF1-DEPENDENT SIGNALING AND FUNCTIONS

(75) Inventors: Mindy Tsai, Palo Alto, CA (US); See-Ying Tam, Palo Alto, CA (US); Stephen J. Galli, Portola Valley, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 80 days.

(21) Appl. No.: 11/158,655

(22) Filed: Jun. 21, 2005

(65) Prior Publication Data

US 2006/0037089 A1 Feb. 16, 2006

Related U.S. Application Data

(60) Provisional application No. 60/582,755, filed on Jun. 24, 2004.

(51) Int. Cl.
*A01K 67/027* (2006.01)
*A01K 67/033* (2006.01)
*G01N 33/00* (2006.01)

(52) U.S. Cl. .......................... 800/18; 800/13; 800/14; 800/3

(58) Field of Classification Search .................... None
See application file for complete search history.

(56) References Cited

U.S. PATENT DOCUMENTS 5,464,764 A * 11/1995 Capecchi et al. ............. 435/6
6,500,942 B1 12/2002 Tam et al.

OTHER PUBLICATIONS

Capeccehi, MR. Science 244:1288-1292, 1989.*
Tam, SY, et al. Nature Immunology 5(8):844-852, 2004.*
Sigmond, C. Art Thromb Vasc Biol 20:1425-1429, 2000.*
Mullins, JJ and LJ Mullins. Hypertension 22:630-633, 1993.*
Niemann, H. ransgenci Res 7:73-75, 1998.*
Kappel, CA et al. Curr Opin Biotech 3:548-553, 1992.*
Mullins, LJ and JJ Mullins. J Clin Invest 98(11):S37-S40, 1996.*
Houdebine, LM. J Biotech 34:269-287, 1994.*
Wall, RJ. Theriogenology 45:57-68, 1996.*
Cameron, ER. Molec Biotech 7:253-265, 1997.*
Horiuchi et al., A Novel RAB5 GDP/GTP Exchange Factor Complexed to Rabaptin-5 Links Nucleotide Exchange to Effector Recruitment and Function, NP_777016, Cell, 1997, 90(6): 1149-1159.
Katayama et al., Antisense Transcription in the Mammalian Tran Scriptome, NP_064367, Science, 2005, 309(5740): 1564-1566.
Mattera et al., Divalent Interaction of the GGAs With the Rabaptin-5 Rabex-5 Complex, NP_055319, Embo J., 2003, 22(1): 78-88.
Stausberg et al., Generation and Initial Analysis of More Than 15,000 Full-Length Human and Mouse CDNA Sequences, NP_957137, Proc. Natl. Acad. Sci., 2002, 99(26): 16899-16903.
Genbank Accession No. XP_341068, This record is predicted by automated computational analysis. This record is derived from an annotated genomic sequence(NW_047374) using gene prediction method: GNOMON, supported by mRNA evidence, Apr. 15, 2005.

* cited by examiner

*Primary Examiner*—Peter Paras, Jr.
*Assistant Examiner*—Marcia S. Noble
(74) *Attorney, Agent, or Firm*—Bozicevic, Field & Francis LLP; Pamela J. Sherwood

(57) ABSTRACT

Non-human transgenic animal models and cells derived therefrom are provided for RabGEF1 function. RabGEF1 is a negative regulator of FcεRI-dependent mast cell activation and T cell activation via the T cell receptor and a lack of RabGEF1 results in the development of skin inflammation in vivo. The mast cells derived from such animals exhibit enhanced Ras-mediated signaling and functional responses when activated through high affinity IgE receptors. These cells show significant potentiation of IgE and antigen-dependent secretion of 3 classes of mast cell mediators, providing a useful source of mast cells for screening assays. The animals and cells derived therefrom are also useful for screening biologically active agents that may modulate RabGEF1 function, including therapeutic agents for the treatment of skin disorders, such as eczema, psoriasis, and the like, or for the treatment of other mast cell-associated disorders, including allergic disorders, such as asthma and hay fever, and certain autoimmune disorders, such as rheumatoid arthritis and multiple sclerosis. Inhibiting RabGEF1 function may be useful in those conditions in which it is desirable to enhance T cell and/or mast cell function, such as in AIDS or other immune deficiency disorders.

2 Claims, 15 Drawing Sheets

FIG. 2A

```
Mouse RabGEF1  227  ETTDDEKKDL AIQKRIRALH WVTPQMLCVP VNEEIPEVSD MVVKAITDII
Yeast Vps9p    157  EHMKDLTNDD TLLEKIRHYR FISPIMLDIP DTMPNARLNK FVHLASKELG
Human RIN1     448  RLAADG-SLG RLAEGLRLAR AQGPGAFGSH LSLPSPVE-- -LEQVRQKLL
Human JC265    182  FHMADG-SWK QLKENLQLVR QRNPQELGVF APTPDFVD-- -VEKIKVKFM Mouse RabGEF1  277  EMDSKRVPRD KLACITRCSK HIFNAIKITK NEPASADDFL PTLIYIVLKG
Yeast Vps9p    207  KINRFKSPRD KMVCVLNASK VIFGLLKHTK LEQNGADSFI PVLIYCILKG
Human RIN1     494  QLVRTYSPSA QVKRLLQACK LLYMALRTQE GEGSGADGFL PLLSLVLAHC
Human JC265    228  TMQKMYSPEK KVMLLLRVCK LIYTVMENNS GRMYGADDFL PVLTYVIAQC
                                       LL  CK LIY         GAD FL PVL
                                         MOTIF I            MOTIF II Mouse RabGEF1  327  NPPRLQSNIQ YITRFCNPSR LMTGEDGYYF TNLCCAVAFI EKLDAQSL
Yeast Vps9p    257  QVRYLVSNVN YIERFRSPDF I-RGEEEYYL SSLQAALNFI MSLTERSL
Human RIN1     544  DLPELLLEAE YMSELLEPSL L-TGEGGYYL TSLSASLALL SGLGQAHT
Human JC265    278  DMLELDTEIE YMMELLDPSL L-HGEGGYYL TSAYGALSLI KNFQEEQA
                                          GE  YYL TS
                                           MOTIF III
```

FIG. 2B

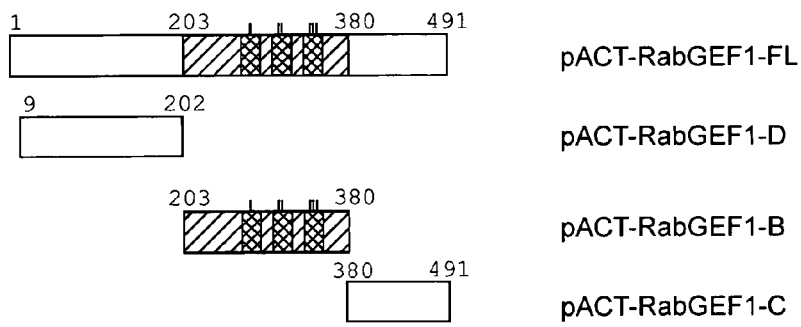

| DNA-binding hybrid | Activation domain hybrid | Colony color | Relative β-Gal units |
|---|---|---|---|
| pAS2-mHRas | pACT-RabGEF1-FL | Blue | 229 |
| pAS2-mHRas | pACT-RabGEF1-D | Blue | 14 |
| pAS2-mHRas | pACT-RabGEF1-B | Blue | 24 |
| pAS2-mHRas | pACT-RabGEF1-C | Blue | 138 |
| pAS2-yRas2p | pACT-RabGEF1-FL | White | 6 |
| pAS2-yRas2p | pACT-RabGEF1-D | White | 4 |
| pAS2-yRas2p | pACT-RabGEF1-B | White | <1 |
| pAS2-yRas2p | pACT-RabGEF1-C | White | <1 |

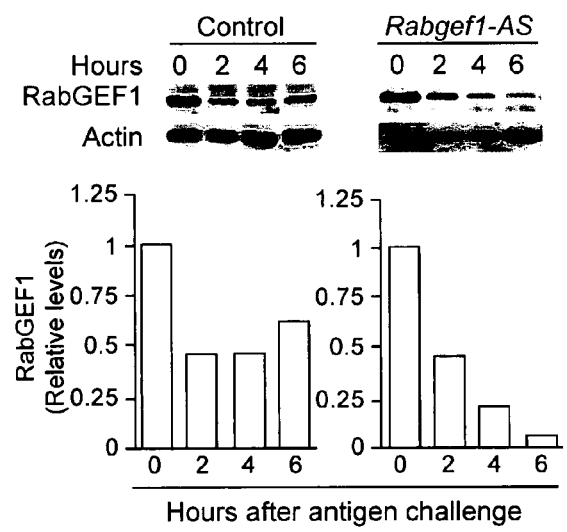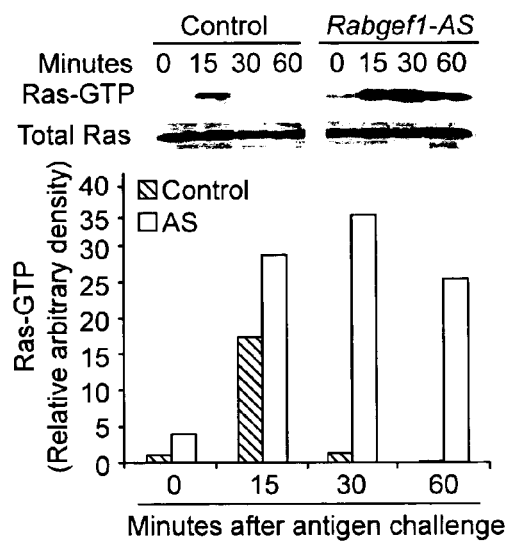
FIG. 3A
FIG. 3B

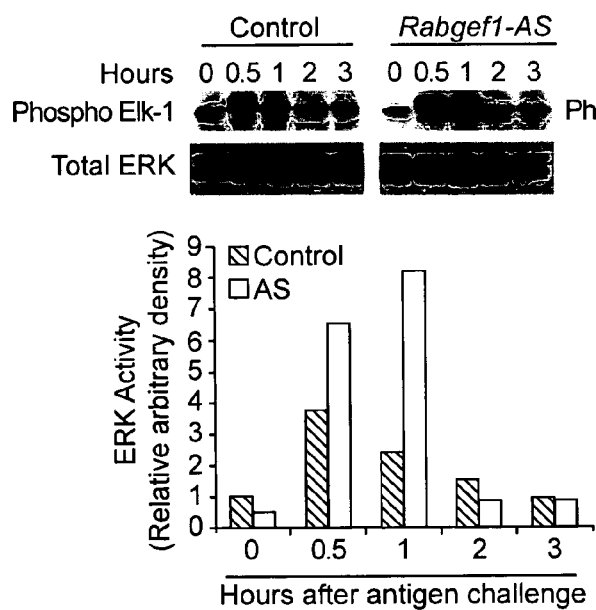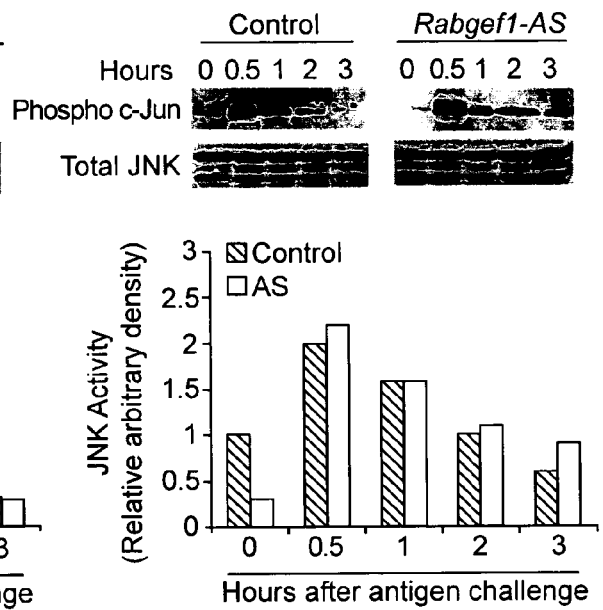

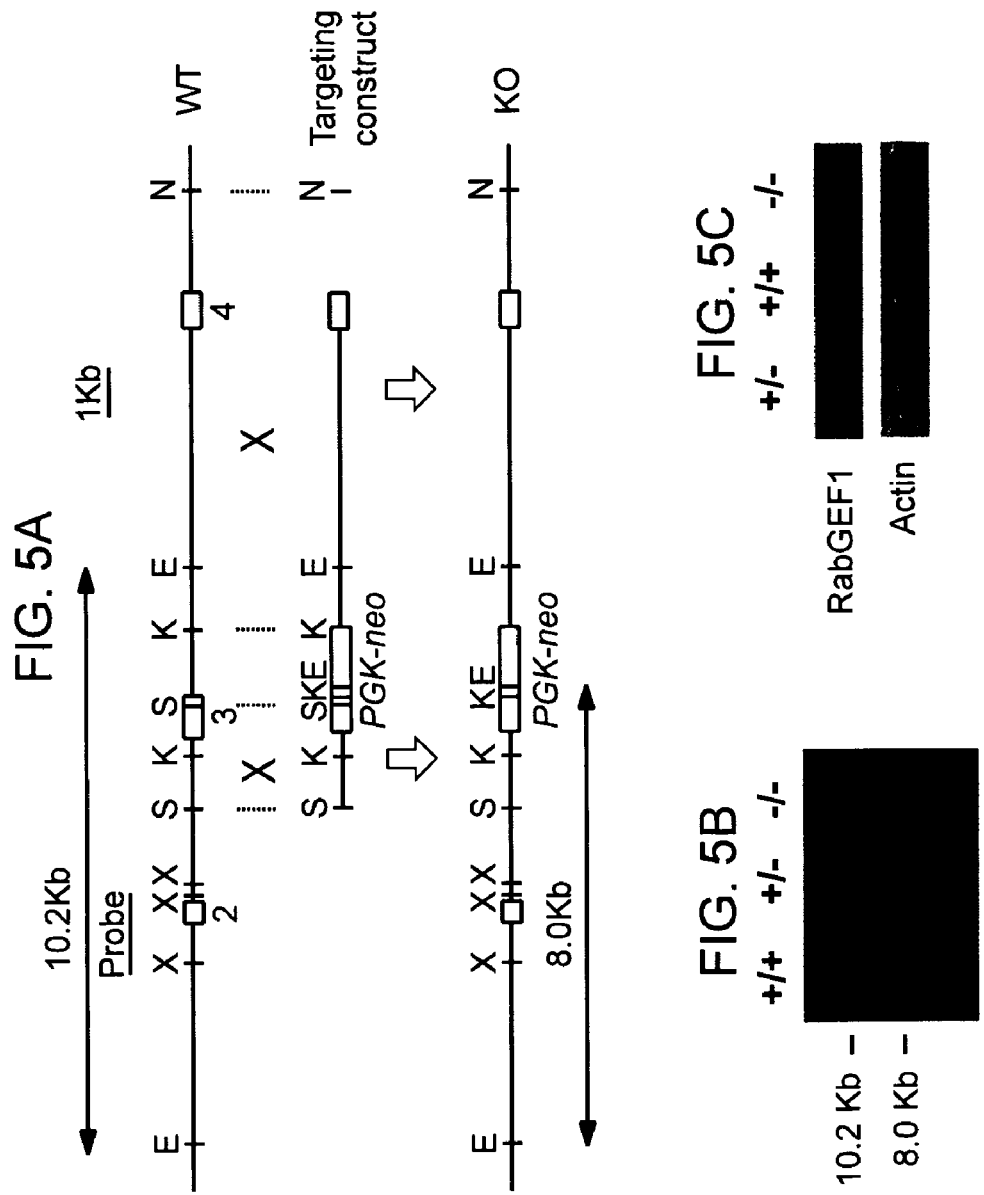

Minutes after antigen challenge

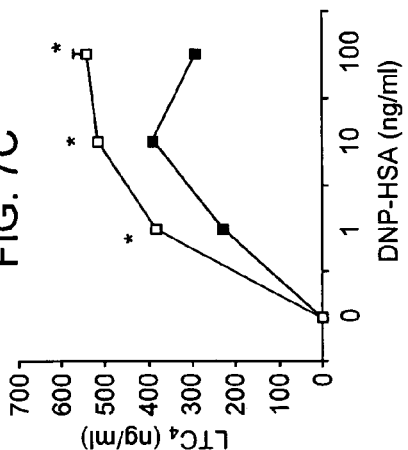
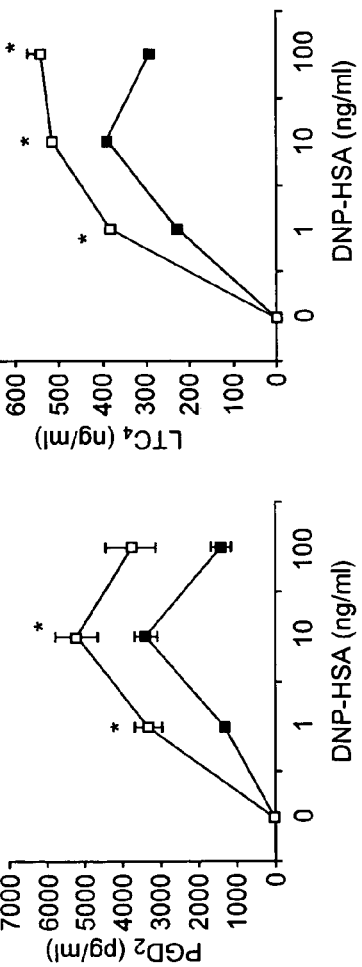
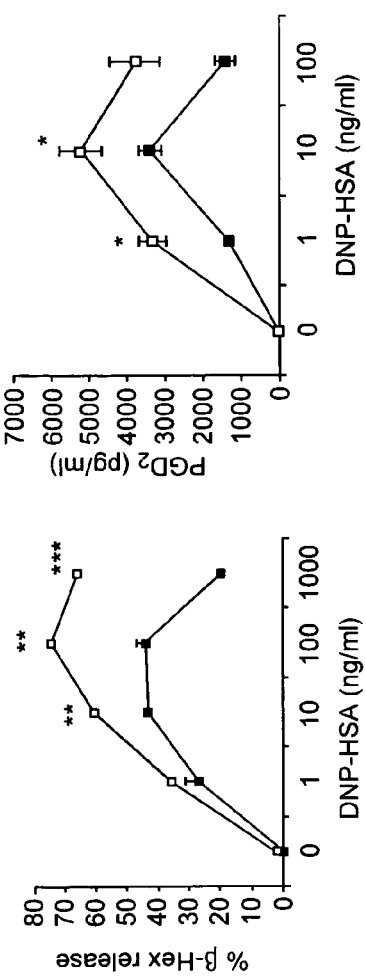
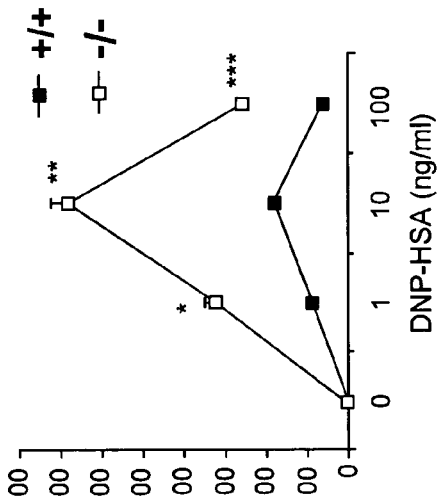
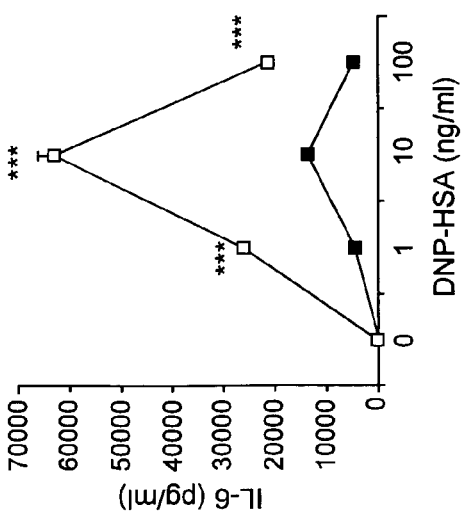

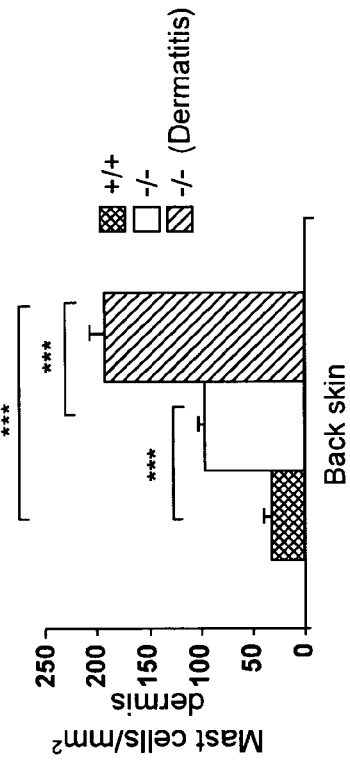
FIG. 8B
FIG. 8C
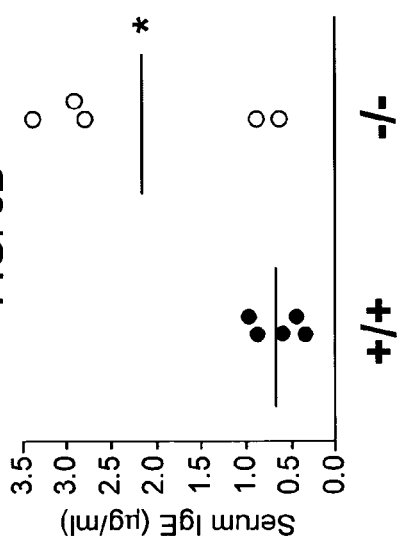
FIG. 8D
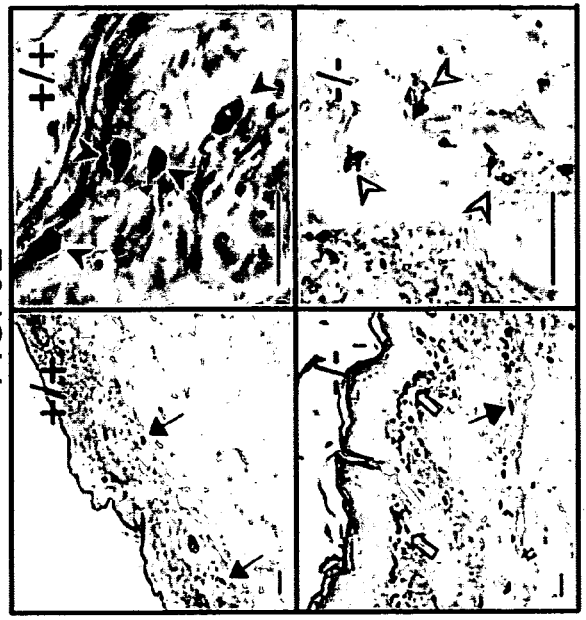
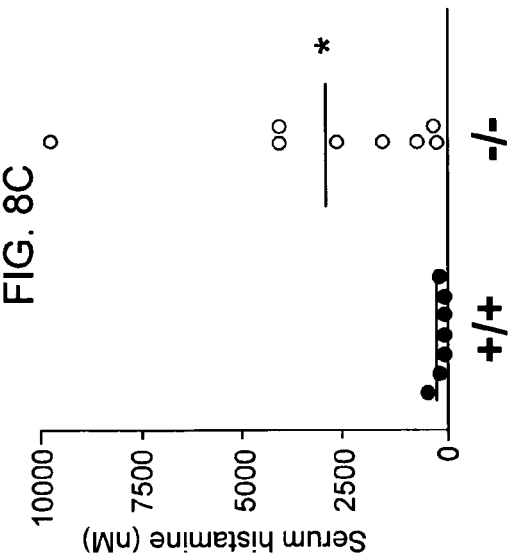
FIG. 8E ized by the aggregation of FcεRI. This FcεRI-dependent activation results in degranulation (secretion of preformed mediators that are stored in the cytoplasmic granules, such as histamine, the synthesis and release of lipid mediators, including prostaglandin $D_2$ ($PGD_2$) and leukotriene $C_4$ ($LTC_4$), the de novo synthesis of proinflammatory lipid mediators, and the synthesis and secretion of cytokines and chemokines. In addition to these IgE/antigen-induced activation events, IgE binding to FcεRI in the absence of a specific antigen induces the up-regulation of FcεRI surface expression in mast cells and basophils and the prolonged survival of mouse mast cells under growth factor-limiting conditions. In mast cells, the activation of Ras-mediated protein kinase cascades is required for the expression of optimal immunologically-specific function when cell activation is initiated by antigen- and IgE-dependent aggregation of FcεRI.

IN VIVO MODELS FOR RABGEF1-DEPENDENT SIGNALING AND FUNCTIONS

This invention was made with Government support under contract R37AI23990 awarded by the National Institutes of Health. The Government has certain rights in this invention.

BACKGROUND OF THE INVENTION

Mast cells are major effector cells for immediate hypersensitivity and allergic diseases. In these settings, mast cell activation by IgE antibody and antigen contributes to pathology, such as in anaphylaxis, asthma, hay fever and atopic dermatitis or eczema. Activation of mast cells by other mechanisms is also thought to contribute to many other diseases, including certain autoimmune diseases such as rheumatoid arthritis and multiple sclerosis. In host defense against pathogens, including some parasites and bacteria, mast cell activation can contribute to health by promoting clearance of the pathogen.

In allergic diseases, cross-linking of IgE bound to its high-affinity receptor, FcεRI, with multivalent antigen initiates the activation of mast cells by promoting the aggregation of FcεRI. This FcεRI-dependent activation results in degranulation (secretion of preformed mediators that are stored in the cytoplasmic granules, such as histamine, the synthesis and release of lipid mediators, including prostaglandin $D_2$ ($PGD_2$) and leukotriene $C_4$ ($LTC_4$), the de novo synthesis of proinflammatory lipid mediators, and the synthesis and secretion of cytokines and chemokines. In addition to these IgE/antigen-induced activation events, IgE binding to FcεRI in the absence of a specific antigen induces the up-regulation of FcεRI surface expression in mast cells and basophils and the prolonged survival of mouse mast cells under growth factor-limiting conditions. In mast cells, the activation of Ras-mediated protein kinase cascades is required for the expression of optimal immunologically-specific function when cell activation is initiated by antigen- and IgE-dependent aggregation of FcεRI.

Knowledge of the signaling pathways that result in the FcεRI-dependent secretion of mast cell mediators is increasing. In mast cells and basophils, the FcεRI receptor is a tetrameric complex comprised of a single 45 kDa α chain, which binds the Fc portion of IgE, a single 30 kDa β chain, and a homodimer of two 10 kDa γ chains. Aggregation of FcεRI activates Lyn, a Src family protein-tyrosine kinase that is constitutively associated with the β subunit. Activated Lyn then phosphorylates the immunoreceptor tyrosine-based activation motifs (ITAMs) of the β and γ subunits, inducing the recruitment and activation of Syk, which phosphorylates multiple substrates, including linker for activation of T cells (LAT) and phospholipase C-γ (PLC-γ). This results in the activation of two downstream cascades: the PLC-γ/protein kinase C cascade, required for degranulation and the release of mediators stored in the cells' cytoplasmic granules, and the Ras/ERK/phospholipase $A_2$ cascade, critical for the release of cytokines and arachidonic acid.

Ras proteins are small GTPases important in the control of cell activation, proliferation and differentiation in diverse cell types. The mechanism by which Ras regulates such processes, through interactions with other intracellular molecules, is quite complex. Ras proteins are membrane-associated proteins that cycle between an active GTP-bound form and an inactive GDP-bound form. Conversion of the inactive GDP-bound Ras to the active GTP-bound state, e.g., when Ras guanine nucleotide exchange factors (GEFs) are recruited to the plasma membrane in response to an appropriate extracellular signal, relays responses initiated at the cell surface to multiple downstream signaling cascades. Ras can bind directly to the key effector Raf-1 to initiate activation of the ERK mitogen-activated protein (MAP) kinase cascade. However, Ras regulates a wide spectrum of cellular responses, and multiple effectors are required to mediate the many potential biological actions of Ras. Indeed, a diverse group of structurally and functionally distinct candidate Ras effectors in addition to Raf-1 have been identified, including GEFs for Ral, Ras GTPase-activating proteins (GAPs) such as p120 GAP and neurofibromin (NF1), MEKK1, AF6, phosphatidylinositol-3-kinase (PI3K), RIN1.

Many different receptors expressed on the surface of diverse cell types can result in the activation of signal transduction pathways that are importantly influenced by Ras, and these pathways in turn determine whether, and to what extent, these cells respond to such cell surface receptor-dependent activation by proliferating, differentiating (i.e., developing new functional characteristics), and/or expressing specific functions. Depending on the circumstances, these "down-stream" consequences of the activation of Ras-dependent signal transduction pathways can have either adaptive (physiological) or maladaptive (pathological) consequences. Appropriate Ras-dependent mast cell secretion of histamine, serotonin, cytokines and other mediators can be important for host defense against parasites and other pathogens, whereas the inappropriate activation of these same pathways, for example, by a reaction to a bee-sting in patients who are allergic to components of bee venom, can lead to fatal anaphylaxis. Thus, Ras also represents an important element of signaling pathways that regulate the development and/or function of many cell types besides mast cells, including T cells, B cells, epithelial cells and nerve cells. (Ras represents a major regulator of many of the most fundamental biological processes involved in both health and disease.

SUMMARY OF THE INVENTION

Non-human transgenic animal models and cells derived therefrom are provided for RabGEF1 function, where the transgenic animal is characterized by having an altered RabGEF1 gene. The transgenic animals may be either homozygous or heterozygous for the alteration. Isolated cells of interest may include T cell, mast cells, epithelial cells (such as the keratinocytes that form the surface of the skin) and other cells in which RabGEF1 is normally expressed. Alterations to the RabGEF1 gene in the transgenic animals and cells include deletions or other loss of function mutations, introduction of an exogenous gene having a nucleotide sequence with targeted or random mutations, introduction of an exogenous gene from another species, or a combination thereof. RabGEF1 is a negative regulator of FcεRI-dependent mast cell activation, and of other ras-mediated signaling.

Mast cell activation induced by aggregation of FcεRI receptors with IgE and antigen is mediated through the activation of multiple protein kinase cascades. RabGEF1-deficient mast cells exhibit enhanced levels of degranulation (with release of histamine and other granule contents) and release of lipid mediators (such as leukotrienes and prostaglandins) and cytokines (including interleukin-6 [IL-6] and tumor necrosis factor-α (TNF-α]) in response to FcεRI aggregation. The animals and cells derived therefrom are useful for screening biologically active agents that may modulate RabGEF1 function, including therapeutic agents for the treatment of skin disorders, such as eczema (also called atopic dermatitis), psoriasis, and the like, or for the treatment of allergic disorders such as asthma and hay fever (allergic rhinitis).

In one embodiment of the invention, the transgenic animals have a pattern of immunological dysfunction of severe skin inflammation and increased numbers of mast cells. These animals find use, for example, as a model for atopic dermatitis, and in screening for agents that are therapeutic for atopic dermatitis or psoriasis. The skin inflammation first appears as raised scaling plaques about the ears and face, spreading to the neck and back. Histological examination reveals epidermal hyperplasia, with hyperkeratinosis and prominent psoriasiform cutaneous inflammation accompanied by increased vascularity. At the sites of severe inflammation, the mast cell numbers are strikingly higher and some mast cells exhibit signs of cell activation and/or degranulation.

The mast cells derived from such animals exhibit enhanced Ras-mediated signaling and functional responses when activated through high affinity IgE receptors. These cells show significant potentiation of IgE and antigen-dependent secretion of mast cell mediators, providing a useful source of mast cells for screening assays.

BRIEF DESCRIPTION OF THE FIGURES

FIG. 2A-2C. Homology of RabGEF1 with members of a Rab5 binding protein family and direct interaction of RabGEF1 with Ras. (a) Alignment of amino acid sequences of mouse RabGEF1 (SEC ID NO:5) with the Vps9p domains of Vps9p (SEC ID NO:6), Rin1, (SEC ID NO:7), and JC265(SEC ID NO:8). The Vps9p domains of Vps9p, RIN1, and JC265 and the proposed GBH motifs I(SEC ID NO:9), II(SEC ID NO:10), and III(SEC ID NO:11) illustrated here represent those previously described. Identical amino acids or conservative substitutions present in three or four proteins are shaded. Conservative substitutions for the alignment are defined as follows: V, L, I and M; K, R and H; F, Y and W; D and E; N and Q; S and T; G and A. (b) Interactions of mouse RabGEF1 with mouse H-Ras protein or yeast Ras2p protein in the yeast two-hybrid assay. Different segments of the mouse RabGEF1 protein (shaded areas are Vps9p domains; black areas are putative GBH motifs) were expressed as GAL-4 activation domain fusion proteins, whereas the mouse H-Ras and yeast Ras2p proteins were expressed as DNA-binding fusion proteins. Positive interactions were assessed with both a qualitative colony-lift β-galactosidase filter assay using X-gal as the substrate (Colony color) and a quantitative liquid culture β-galactosidase assay using chlorophenol red-β-D-galactopyranoside as the substrate (Relative β-Gal units). (c) Binding of RabGEF1 to activated Ras in mast cells activated by FcεRI aggregation. CI.MC/C57.1 mast cells were stimulated with IgE and antigen to induce FcεRI aggregation, and cell lysates were subjected to immunoprecipitation using the GST-fusion protein containing the Ras binding domain (RBD) of Raf1. The pulled-down RabGEF1 was detected using an anti-RabGEF1 antibody. Blots were stripped and probed with an anti-Ras antibody to detect Ras-GTP in the same immunoprecipitate.

FIG. 3A-3D. Potentiation of Ras-mediated signaling responses in CI.MC/C57.1 mast cells transfected with the Rabgef1 antisense expression vector in response to FcεRI-dependent cell activation. (a) Western blot analysis showing the kinetics of RabGEF1 protein expression in response to FcεRI aggregation, performed as in FIG. 1, in a selected antisense. (Rabgef1-AS) transfectant (T8A2) and in its respective CMV vector control (Control) transfectant (T8C2). Blots were stripped and probed with an anti-actin antibody to show equal loading of proteins in each lane. (b) Kinetics of Ras activation induced by FcεRI aggregation, performed as in FIG. 1, in Rabgef1-AS or Control transfectants. Activated Ras was immunoprecipitated using GST-fusion protein containing RBD of Raf-1. The pulled-down Ras-GTP was detected using an anti-Ras antibody. (c) Kinetics of ERK activation induced by FcεRI aggregation in Rabgef1-AS or Control transfectants. Phospho-ERK was immunoprecipitated using an anti-phospho-p44/42 MAP kinase monoclonal antibody, and the phosphorylation of Elk-1 by ERK was detected using an anti-phospho-Elk-1 antibody. (d) Kinetics of JNK activation induced by FcεRI aggregation in Rabgef1-AS or Control transfectants. JNK was immunoprecipitated using a c-Jun GST-fusion protein, and the phosphorylation of the c-Jun GST-fusion protein by JNK was detected using an anti-phospho-c-Jun antibody. Findings illustrated in (a)-(d) are representative of those obtained with 4 different pairs of AS and control transfectants. Each experiment in (a)-(d) was repeated 3-4 times, all of which gave similar results. All signals were quantified by densitometric scanning.

FIG. 5A-5C. Generation and analysis of $Rabgef1^{-/-}$ mice. (a) The Rabgef1 gene locus and targeting construct. Exons 2, 3 and 4, encoding part of the 5' terminus of RabGEF1, are illustrated. The 1.2 kb XbaI fragment probe, containing the entire exon 2, hybridizes to a 10.2 kb SpeI restriction fragment in the wild-type germline locus and to a 8.0 kb SpeI fragment in the germline locus of the correctly targeted animals. K, KpnI; N, NheI; E, SpeI; S, StuI; X, XbaI; PGK-neo, phosphoglycerate kinase gene promoter/neomycin-resistance gene cassette. Restriction sites that were destroyed after subcloning into the pLNL targeting vector are illustrated in red. (b) Southern blot analysis. Genomic DNAs extracted from the tails of $Rabgef1^{-/-}$, $Rabgef1^{+/-}$, and $Rabgef1^{+/+}$ animals were digested with SpeI and hybridized with the radiolabeled exon 2 probe. (c) Western blot analysis of RabGEF1 protein levels in BMCMCs derived from $Rabgef1^{-/-}$, $Rabgef1^{+/-}$, and $Rabgef1^{+/+}$ animals. Blots were stripped and re-probed with an anti-actin antibody.

FIG. 7A-7E. Enhanced release of mediators and cytokines in $Rabgef1^{-/-}$ BMCMCs in response to FcεRI-dependent cell activation. (a) Release of β-Hexoseaminidase (β-Hex, a mediator stored in the mast cells' cytoplasmic granules) induced by FcεRI aggregation from $Rabgef1^{-/-}$ vs. wild-type BMCMCs. Cells were sensitized with anti-DNP IgE mAb overnight and then challenged with different concentrations of DNP-HSA as illustrated. Specific release of β-Hex was measured one hour after antigen challenge. (b,c) Release of prostaglandin $D_2$ ($PGD_2$) (b) and leukotriene $C_4$ ($LTC_4$) (c) induced by FcεRI aggregation, as in (a), from $Rabgef1^{-/-}$ (−/−) vs. wild-type (+/+) BMCMCs. Levels of $PGD_2$ and $LTC_4$ were measured one hour after antigen challenge using enzyme immunoassays. (d,e) Release of IL-6 (d) or TNF-α (e) induced by FcεRI aggregation, as in (a), from $Rabgef1^{-/-}$ (−/−) vs. wild-type (+/+) BMCMCs. Cytokine levels were measured by ELISA assays 6 hours after antigen challenge. Values shown represent the mean±SEM of duplicate determinations and are representative of 3-4 separate experiments. *$p<0.05$; $p<0.01$; *$p<0.001$ vs. wild-type controls by unpaired Student's t test.

FIG. 8A-8E. Phenotypic characteristics of $Rabgef1^{-/-}$ (−/−) vs. wild-type (+/+) mice. (a) Histological analysis of skin of 12 weeks old $Rabgef1^{-/-}$ and wild type mice. The skin of the wild-type mouse (+/+) was unremarkable, whereas that of a homozygous $Rabgef1^{-/-}$ mouse (−/−) exhibited epidermal hyperplasia with hyperkeratosis (note great difference in the thickness of the epidermis [e] in the skin of the $Rabgef1^{-/-}$ vs. wild-type mouse), dermal inflammation (*), and micro-abscess formation [arrows] in the epidermis. Scale bars=75 μm. (b) $Rabgef1^{-/-}$ mice exhibited increased serum IgE levels. Serum IgE levels were measured by ELISA. *$p<0.05$ vs. levels in wild-type controls by unpaired Student's t test. (c) $Rabgef1^{-/-}$ mice exhibited increased levels of serum histamine. Serum histamine levels were measured by an EIA kit. *$p<0.05$ vs. wild-type levels in controls by unpaired Student's t test. (d) $Rabgef1^{-/-}$ mice exhibited increased mast cell numbers in the back skin. Skin mast cells were stained with toluidine blue and counted by morphometry. Highest numbers of mast cells were detected at sites of clinically observable skin inflammation (dermatitis) in $Rabgef1^{-/-}$ mice, as compared to skin with no grossly observable inflammation in $Rabgef1^{-/-}$ mice and to skin of the wild-type mice. All mice were 6-12 weeks old at the time of analysis for skin mast cell numbers. ***$p<0.001$ for the comparisons shown by unpaired Student's t test. (e) Histological analysis of mast cells in skin of $Rabgef1^{-/-}$ mice. Skin mast cells were stained with toluidine blue. Mast cells (purple stained cells—indicated by arrows and arrowheads) are especially abundant just beneath the dermal-epidermal junction in the −/− mouse skin (open arrows). At high magnification, the mast cells in +/+ skin exhibit intensely stained, abundant cytoplasmic granules (closed arrowheads) whereas many mast cells in −/− skin exhibit granules that appear to be dispersed at some distance from the main part of the of the cells (open arrowheads). Scale bars=75 μm.

DESCRIPTION OF THE SPECIFIC EMBODIMENTS

Figure 1B:
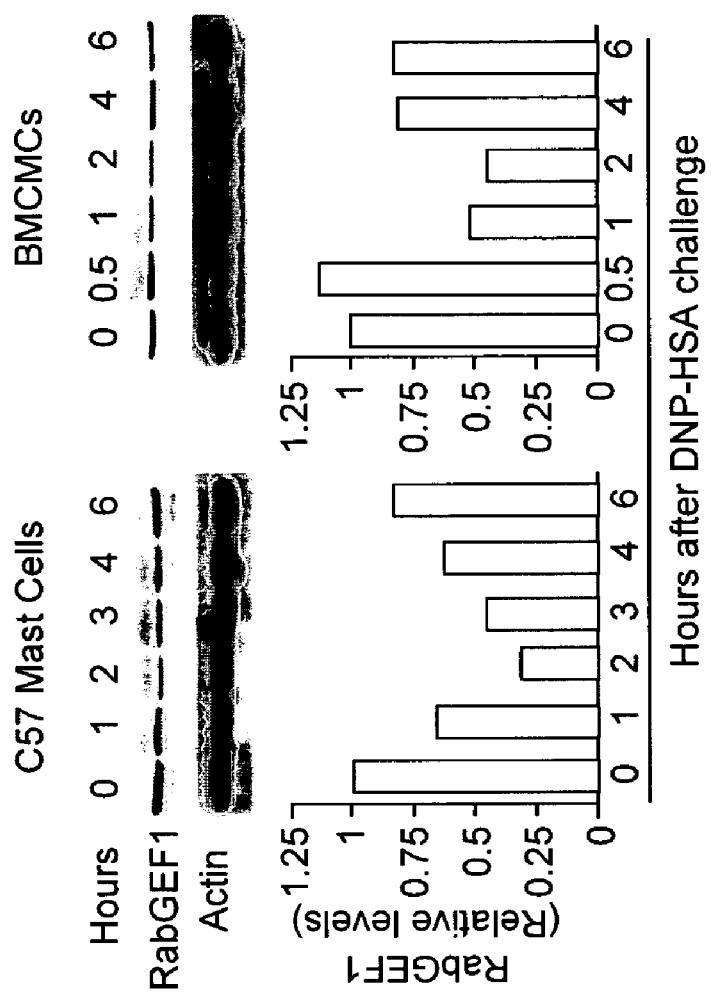
FIG. 1A-1B. Expression of RabGEF1 in mouse mast cells activated by FcεRI aggregation in vitro. (a) Rabgef1 mRNA expression in BMCMCs stimulated by FcεRI aggregation. BMCMCs were sensitized for 2 hours at 37° C. with an anti-DNP IgE mAb and then challenged with $DNP_{30-40}HSA$ (50 ng/ml) for the various time intervals indicated. Northern analysis was performed with 20 μg of total RNA hybridized with the band 60-4 (Rabgef1) cDNA probe. Ethidium bromide-stained agarose gel shows equal loading of RNA in each lane. (b) RabGEF1 protein expression in mouse mast cells stimulated by FcεRI aggregation. Western blot analysis shows that activation via FcεRI aggregation induced a transient decrease in RabGEF1 protein levels in CI.MC/C57.1 (C57) mast cells and in BMCMCs. Blots were stripped and probed with an anti-actin antibody to show equal loading of proteins in each lane. Findings illustrated in (a) and (b) are representative of those obtained with 3-4 separate determinations, all of which gave similar results. All signals in (b) were quantified by densitometric scanning.

Non-human transgenic animal models and cells derived therefrom are provided. The animals have altered forms of the RabGEF1 gene. Alterations to the gene include deletion or other loss of function mutations, introduction of an exogenous gene having a nucleotide sequence with targeted or random mutations, introduction of an exogenous gene from another species, or a combination thereof. The transgenic animals may be either homozygous or heterozygous for the genetic alteration.

The cells and animals are useful as a model for skin diseases having an inflammatory component, e.g. eczema, psoriasis, dermatitis, etc. The present invention can be applied to the identification of compounds that inhibit or alter mast cell activation. Such compounds have utility in the treatment of allergy and asthma, where mast cell products mediate disease pathology. The subject animals are useful for testing the specificity of drugs developed as RabGEF1-selective agonists and antagonists, and for analysis of Ras signaling pathways. Mammalian species useful as transgenics and as a source for the mast cell lines include canines; felines; equines; bovines; ovines; etc. and primates. Animal models, particularly small mammals, e.g. mouse, rat, rabbit, guinea pig, etc. are particularly useful for experimental investigations.

RabGEF1. RabGEF1 encodes a protein of predicted molecular mass of approximately 60 kDa which shares significant homology to a class of Ras-binding proteins represented by JC265, Rin1 and Vps9p. The terms "RabGEF1 gene" is used generically to designate RabGEF1 genes, e.g. homologs from rat, human, mouse, guinea pig, etc., and their alternate forms. The gene is also intended to mean the open reading frame encoding specific polypeptides, introns, and adjacent 5' and 3' non-coding nucleotide sequences involved in the regulation of expression, up to about 1 kb beyond the coding region, but possibly further in either direction. The DNA sequences encoding RabGEF1 may be cDNA or genomic DNA or a fragment thereof. The gene may be introduced into an appropriate vector for extrachromosomal maintenance or for integration into the host.

The sequence of RabGEF1 has been characterized for a number of species, and is available in public databases, including the mouse (Genbank accession number AF_093590 NP_064367.1); human (Genbank accession number NP_055319.1); rat (Genbank accession number XP_341068.1); bovine (Genbank accession number NP_777016.1) and zebra fish (Genbank accession number NP_957137.1). RabGEF1 down-regulates the functional responses elicited by Ras-dependent signaling pathways, including the functional responses elicited by FcϵRI aggregation in mast cells and down-regulating the amounts of preformed mediator (e.g., -Hex, serotonin) and lipid mediators (e.g., $PGD_2$ and $LTC_4$) and cytokines (e.g., IL-6, TNF-α) released from these cells upon FcϵRI-dependent stimulation.

Expression of RabGEF1 is rapidly increased in mast cells activated through FcϵRI. Expression of RabGEF1 is also increased in mast cells stimulated via activation of their major growth factor receptor (i.e., c-kit); in PC12 adrenal pheochromocytoma cells activated via the receptor for nerve growth factor (NGF) (i.e., TrkA); and in T cells activated via the T cell receptor (TCR), indicating that RabGEF1 is a general negative regulator/effector of Ras and Ras-dependent signaling pathways in diverse cell types which have been activated via distinct cell surface receptors.

The RabGEF1 sequence, including flanking promoter regions and coding regions, may be mutated in various ways known in the art to generate targeted changes in promoter strength, sequence of the encoded protein, etc. The sequence changes may be substitutions, insertions or deletions. Deletions may include large changes, such as deletions of a domain or exon. Other modifications of interest include epitope tagging, e.g. with the FLAG system, HA, etc. For studies of subcellular localization, fusion proteins with green fluorescent proteins (GFP) may be used. Such mutated genes may be used to study structure-function relationships of RabGEF1 polypeptides, or to alter properties of the proteins that affect their function or regulation.

Techniques for in vitro mutagenesis of cloned genes are known. Examples of protocols for scanning mutations may be found in Gustin et al., 1993 Biotechniques 14:22; Barany, 1985 Gene 37:111-23; Colicelli et al., 1985 Mol Gen Genet 199:537-9; and Prentki et al., 1984 Gene 29:303-13. Methods for site specific mutagenesis can be found in Sambrook et al., 1989 Molecular Cloning: A Laboratory Manual, CSH Press, pp. 15.3-15.108; Weiner et al., 1993 Gene 126:35-41; Sayers et al., 1992 Biotechniques 13:592-6; Jones and Winistorfer, 1992 Biotechniques 12:528-30; Barton et al., 1990 Nucleic Acids Res 18:7349-55; Marotti and Tomich, 1989 Gene Anal Tech 6:67-70; and Zhu 1989 Anal Biochem 177:120-4.

Transgenic Animals

The term "transgene" is used herein to describe genetic material that has been or is about to be artificially inserted into the genome of a mammalian cell, particularly a mammalian cell of a living animal. The transgene is used to transform a cell, meaning that a permanent or transient genetic change, preferably a permanent genetic change, is induced in a cell following incorporation of exogenous DNA. A permanent genetic change is generally achieved by introduction of the DNA into the genome of the cell. Vectors for stable integration include plasmids, retroviruses and other animal viruses, YACs, and the like.

Transgenic animals comprise an exogenous nucleic acid sequence present as an extrachromosomal element or stably integrated in all or a portion of its cells, especially in germ cells. Unless otherwise indicated, it will be assumed that a transgenic animal comprises stable changes to the germline sequence. During the initial construction of the animal, "chimeras" or "chimeric animals" are generated, in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

Transgenic animals fall into two groups, colloquially termed "knockouts" and "knockins". In the present invention, knockouts have a partial or complete loss of function in one or both alleles of the endogenous RabGEF1 gene. Knockins have an introduced transgene with altered genetic sequence and function from the endogenous gene. The two may be combined, such that the naturally occurring gene is disabled, and an altered form introduced.

In a knockout, preferably the target gene expression is undetectable or insignificant. A knock-out of a RabGEF1 gene means that functional expression of the RabGEF1 gene has been substantially decreased so that the RabGEF1 protein expression is not detectable or only present at insignificant levels. This may be achieved by a variety of mechanisms, including introduction of a disruption of the coding sequence, e.g. insertion of one or more stop codons, insertion of a DNA fragment, etc., deletion of coding sequence, substitution of stop codons for coding sequence, etc. In some cases the exogenous transgene sequences are ultimately deleted from the genome, leaving a net change to the native sequence. Different approaches may be used to achieve the "knock-out". A chromosomal deletion of all or part of the native gene may be induced, including deletions of the non-coding regions, particularly the promoter region, 3' regulatory sequences, enhancers, or deletions of gene that activate expression of RabGEF1 genes. A functional knock-out may also be achieved by the introduction of an anti-sense construct that blocks expression of the native genes (for example, see Li and Cohen (1996) Cell 85:319-329). "Knock-outs" also include conditional knock-outs, for example where alteration of the target gene occurs upon exposure of the animal to a substance that promotes target gene alteration, introduction of an enzyme that promotes recombination at the target gene site (e.g. Cre in the Cre-lox system), or other method for directing the target gene alteration postnatally.

A "knock-in" of a target gene means an alteration in a host cell genome that results in altered expression or function of the native RabGEF1 gene. Increased (including ectopic) or decreased expression may be achieved by introduction of an additional copy of the target gene, or by operatively inserting a regulatory sequence that provides for enhanced expression of an endogenous copy of the target gene. These changes may be constitutive or conditional, i.e. dependent on the presence of an activator or repressor.

The exogenous gene may be from a different species than the animal host, or is otherwise altered in its coding or non-coding sequence. The introduced gene may be a wild-type gene, naturally occurring polymorphism, or a genetically manipulated sequence, for example having deletions, substitutions or insertions in the coding or non-coding regions. The introduced sequence may encode a RabGEF1 polypeptide, or may utilize the RabGEF1 promoter operably linked to a reporter gene. Where the introduced gene is a coding sequence, it is usually operably linked to a promoter, which may be constitutive or inducible, and other regulatory sequences required for expression in the host animal. By "operably linked" is meant that a DNA sequence and a regulatory sequence(s) are connected in such a way as to permit gene expression when the appropriate molecules, e.g. transcriptional activator proteins, are bound to the regulatory sequence(s).

Specific constructs of interest, but are not limited to, include anti-sense RabGEF1, which will block native RabGEF1 expression, expression of dominant negative RabGEF1 mutations, and over-expression of a RabGEF1 gene. A detectable marker, such as lac Z or green fluorescent protein (GFP) may be introduced into the locus, where upregulation of expression will result in an easily detected change in phenotype. Constructs utilizing the RabGEF1 promoter region, in combination with a reporter gene or with the coding region are also of interest.

A series of small deletions and/or substitutions may be made in the RabGEF1 gene in knock-in transgenic animals to determine the role of different exons in binding to Ras, etc., in the functions of the Vps9p domain, and in the expression of gross and detectable phenotypes in the transgenic animals.

DNA constructs for homologous recombination will comprise at least a portion of the RabGEF1 gene with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990) Methods in Enzymology 185:527-537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture.

Cell Lines

Cells comprising stable genetic mutations of the RabGEF1 sequence may be isolated from transgenic animal(s) as primary cells, or maintained as cell lines. Cells of interest include mast cells, T cells, B cells, epithelial cells, such as keratinocytes of the skin and nerve cells.

The cells of the invention are isolated from tissue, which tissue may be fetal, neonatal, juvenile or adult. Any tissue source of for the cell of interest can be used, including blood, bone marrow, brain, eye, heart, intestine, kidney, liver, lung, lymph node, skin, spleen, and thymus. The unseparated cells may be plated in culture, or an isolation step to enrich for the cells of interest may be employed. An enriched cell population may be about 75% cells of the selected phenotype, more usually at least 90% cells of the selected phenotype. The enriched cell populations may be separated from other cells, e.g. red blood cells, lymphocytes, etc., on the basis of specific markers on the cell surface, which markers are identified with affinity reagents, e.g. monoclonal antibodies; on the basis of differential density after gradient centrifugation, etc. After isolation or enrichment, or after an initial period of culture, the cells are preferably cloned, e.g. by colony formation in semi-solid media, limiting dilution, automated cell deposition, etc.

Mast cells may be isolated from primary sources, or may be generated from progenitor cells in vitro. Myeloid progenitor cells useful for such purposes are well-known in the art, and include CD34+ cells from bone marrow, cord blood, mobilized stem cell populations, and the like. The progenitor cells are cultured by methods known in the art, e.g. in the presence of stem cell factor (SCF), IL-3 and IL-6. Other supplements for derivation of mast cells may include IL-9, IL-10, TPO, FLT-3L, PGE-2, and IgE. Factors useful in stimulating mast cells include IL-4; anti-IgE; the calcium ionophore, A23187; Compound 48/80; Con A; NP-BSA; complement products C3a or C5a, LPS and other bacterial products, substance P and other neuropeptides, immune complexes of IgG, especially, in the mouse, IgG1, etc.

T cells may be obtained, including Th2 type T cells, and particularly human T cells. T cell sources of interest include peripheral blood mononuclear cell preparations, which may be unselected, thereby providing a complex mixture of myeloid and lymphocytic cells, or may be selected for expression of T cell markers, such CD4+, CD3+; etc. Inflammation in chronic Th2 environments, such as asthma, is characterized by the presence of TNF-α, IL-1 and IL-4, but not IFN-γ. Lymphokine-producing activated lymphocytes (CD45RO+, CD44hi, etc.) are a hallmark of inflammatory diseases such as asthma. Depending on the disease environment and tissue site, activated lymphocytes can differ in their expression and function of adhesion molecules and other receptors, as well as in their production of various cytokines and other factors. The ability to selectively block lymphocyte activation associated with the inflammatory disease without inhibiting or suppressing lymphocyte activation associated with the ability to fight infection and neoplasia is a goal of inflammatory drug therapy. Among the factors useful for stimulating T cells for these purposes are IL-2; superantigens, including SEA, SEB, TSST, etc.; anti-CD3; anti-CD28; PHA; ConA; etc.

The selection of culture medium to isolate cells or maintain these cells or their progeny is a matter of routine experimental design and within the ordinary skill in the art. At a minimum, culture media contain a carbon source, a nitrogen source, essential amino acids, vitamins and minerals. Media may be protein- or serum-free or may contain such components as growth factors or serum, as required. A preferred growth medium is media supplemented with FBS, essential and non-essential amino acids, vitamins, 2-ME, penicillin, streptomycin, L-glutamine, Na pyruvate and buffer.

Cells that can be continuously cultured and do not die after a limited number of cell generations are referred to as "immortalized", in contrast to finite primary cultures. Immortalization of cells can occur spontaneously or be chemically or virally induced. The cell lines may optionally be selected for, or transformed to be, growth factor independent, resistant to cell death, resistant to dedifferentiation and/or resistant to senescence.

Immortalization may be associated with transformation and significant changes in phenotype. The altered ability to be continuously cultured may be due to, for example, a deletion or mutation in one or more of the genes whose products play a role in cell division, senescence or death, or overexpression or mutation of one or more oncogenes that override the action of the division, senescence or death genes. Genes that may be transfected or transduced into the cells to enhance immortalization and growth factor independence include polyoma middle T antigen, adenovirus E1A, myc oncogenes, v-rel fusions, and the E6 and E7 genes of human papilloma virus type 16 or 18. Genes that may be transfected or transduced into the cells for resistance to senescence include telomerase. Genes that may be introduced for resistance to programmed cell death include the anti-apoptotic proteins in the bcl-2 family. Vectors suitable for introduction of such genes, and methods for their use, are known in the art.

The cells may be characterized for features of interest, including expression of specific cell surface molecules. Analyses of the cell surface using monoclonal antibodies are made using a flow cytometer (for a review of methods, see Viedma Contreras (1999) *Clin Chem Lab Med.* 37(6):607-22; Maino and Picker (1998) *Cytometry* 34(5):207-15; Drouet and Lees (1993) *Biol Cell.* 78(1-2):73-8. Briefly, the cells are either combined with monoclonal antibodies directly conjugated to fluorochromes, or with unconjugated primary antibody and subsequently with commercially available secondary antibodies conjugated to fluorochromes. The stained cells are analyzed using a flow cytometer (for example as available from Becton Dickinson, Mountain View, Calif.). Additional phenotypic characteristics can be determined by gene expression profiling e.g. by reverse-transcriptase polymerase chain reaction (RT-PCR).

Methods of Use

The cultured cells and transgenic animals may be used in a wide variety of ways, e.g. in gene discovery; for dissection of Ras signaling pathways; for characterization of mast cell interactions with antigen, IgE, other cells, etc.; for screening assays; and the like.

The invention further provides methods of inhibiting the functional responses (e.g., proliferation, functional activation) elicited by activation of Ras-dependent signaling pathways in cells, comprising contacting the cells with an agent that enhances or mimics the activity of RabGEF1 protein. The invention further provides methods of inhibiting the functional responses elicited by FcεRI aggregation, particularly in mast cells, comprising contacting a mast cell population of the invention with a candidate agent that enhances or mimics the activity of RabGEF1. The invention also relates to a method of treating a mammal in need thereof to inhibit such functional responses, comprising administering to a mammal an agent developed during such screening. For example, the invention relates to methods of inhibiting IgE and antigen-dependent release of mediators from mast cells. Such methods can be used to inhibit mediator release from mast cells and other effector cells that express FcεRI, such as basophils, monocytes/macrophages, mast cells, Langerhans' cells and eosinophils, thereby ameliorating disorders such as atopic dermatitis, asthma, hay fever, etc.

The invention further provides methods of enhancing the functional responses (e.g., proliferation, functional activation) elicited by activation of Ras-dependent signaling pathways in cells, comprising contacting the cells with an agent that inhibits or counteracts the activity of RabGEF1 protein. The invention further provides methods of enhancing the functional responses elicited by stimulation of T cells via the T cell receptor (TCR), comprising contacting a T cell population of the invention with a candidate agent that inhibits or counteracts the activity of RabGEF1. The invention also relates to a method of treating a mammal in need thereof to enhance such functional responses, comprising administering to a mammal an agent developed during such screening. For example, the invention relates to methods of enhancing stimulation of T cells via the T cell receptor (TCR). Such methods can be used to enhance the function of T cells and other effector cells that respond to functional activation via Ras-dependent signaling pathways, such as mast cells, basophils, monocytes/macrophages, Langerhans' cells and eosinophils, thereby enhancing the function of T cells and these other cells in settings wherein that is clinically desirable, such as in acquired immunodeficiency disease (AIDS) or other forms of immunosuppression.

Drug Screening Assays

The cells of the present invention may also be used for screening biological response modifiers, i.e. compounds and factors that affect the various Ras signaling pathways, including pathways in mast cells. A wide variety of assays may be used for this purpose, including immunoassays for protein binding; determination of cell growth, differentiation and functional activity; production of hormones; and the like.

For example, the subject cells may be used to screen for molecules that enhance or inhibit mast cell or T cell activation, or the prolonged expression of FcεRI observed with the transgenic animals of the invention. Typically the candidate compound will be added to the cells and/or animal, and the response of the cells monitored through evaluation of cell surface phenotype, functional activity, patterns of gene expression, and the like. Of particular interest are screening assays for agents that have a low toxicity for human cells.

Through use of the subject transgenic animals or cells derived therefrom, one can identify ligands or substrates that bind to, modulate, antagonize or agonize RabGEF1s. Screening to determine drugs that lack effect on these receptors is also of interest. Areas of investigation are the development of treatments for deficiency of RabGEF1, e.g. cancer, atopic dermatitis, atopy, etc. Depending on the particular assay, whole animals may be used, or cell derived therefrom. Cells may be freshly isolated from an animal, or may be immortalized in culture.

The term "agent" as used herein describes any molecule, e.g. protein or pharmaceutical, with the capability of affecting the biological action of RabGEF1. Generally a plurality of assay mixtures are run in parallel with different agent concentrations to obtain a differential response to the various concentrations. Typically, one of these concentrations serves as a negative control, i.e. at zero concentration or below the level of detection. Screening may be directed to known pharmacologically active compounds and chemical analogs thereof.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components is added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

For example, detection may utilize staining of cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

Gene expression in the cells of the invention may be assessed following a candidate treatment or experimental manipulation. The expressed set of genes may be compared with a variety of cells of interest, e.g. dedicated myeloid progenitor cells, immature mast cells, etc., as known in the art. Any suitable qualitative or quantitative methods known in the art for detecting specific mRNAs can be used. mRNA can be detected by, for example, hybridization to a microarray, in situ hybridization in tissue sections, by reverse transcriptase-PCR, or in Northern blots containing poly A+ mRNA. One of skill in the art can readily use these methods to determine differences in the size or amount of mRNA transcripts between two samples. For example, the level of particular mRNAs in mast cells is compared with the expression of the mRNAs in a reference sample.

mRNA expression levels in a sample can be determined by generation of a library of expressed sequence tags (ESTs) from a sample. Enumeration of the relative representation of ESTs within the library can be used to approximate the relative representation of a gene transcript within the starting sample. The results of EST analysis of a test sample can then be compared to EST analysis of a reference sample to determine the relative expression levels of a selected polynucleotide, particularly a polynucleotide corresponding to one or more of the differentially expressed genes described herein.

Alternatively, gene expression in a test sample can be performed using serial analysis of gene expression (SAGE) methodology (Velculescu et al., *Science* (1995) 270:484). In short, SAGE involves the isolation of short unique sequence tags from a specific location within each transcript. The sequence tags are concatenated, cloned, and sequenced. The frequency of particular transcripts within the starting sample is reflected by the number of times the associated sequence tag is encountered with the sequence population.

Gene expression in a test sample can also be analyzed using differential display (DD) methodology. In DD, fragments defined by specific sequence delimiters (e.g., restriction enzyme sites) are used as unique identifiers of genes, coupled with information about fragment length or fragment location within the expressed gene. The relative representation of an expressed gene with a sample can then be estimated based on the relative representation of the fragment associated with that gene within the pool of all possible fragments. Methods and compositions for carrying out DD are well known in the art, see, e.g., U.S. Pat. No. 5,776,683; and U.S. Pat. No. 5,807,680.

Alternatively, gene expression in a sample using hybridization analysis, which is based on the specificity of nucleotide interactions. Oligonucleotides or cDNA can be used to selectively identify or capture DNA or RNA of specific sequence composition, and the amount of RNA or cDNA hybridized to a known capture sequence determined qualitatively or quantitatively, to provide information about the relative representation of a particular message within the pool of cellular messages in a sample. Hybridization analysis can be designed to allow for concurrent screening of the relative expression of hundreds to thousands of genes by using, for example, array-based technologies having high density formats, including filters, microscope slides, or microchips, or solution-based technologies that use spectroscopic analysis (e.g., mass spectrometry). One exemplary use of arrays in the diagnostic methods of the invention is described below in more detail.

In another screening method, the test sample is assayed at the protein level. Methods of analysis may include 2-dimensional gels; mass spectroscopy; analysis of specific cell fraction, e.g. lysosomes; and other proteomics approaches. For example, detection can utilize staining of cells or histological sections (e.g., from a biopsy sample) with labeled antibodies, performed in accordance with conventional methods. Cells can be permeabilized to stain cytoplasmic molecules. In general, antibodies that specifically bind a differentially expressed polypeptide of the invention are added to a sample, and incubated for a period of time sufficient to allow binding to the epitope, usually at least about 10 minutes. The antibody can be detectably labeled for direct detection (e.g., using radioisotopes, enzymes, fluorescers, chemiluminescers, and the like), or can be used in conjunction with a second stage antibody or reagent to detect binding (e.g., biotin with horseradish peroxidase-conjugated avidin, a secondary antibody conjugated to a fluorescent compound, e.g. fluorescein, rhodamine, Texas red, etc.). The absence or presence of antibody binding can be determined by various methods, including flow cytometry of dissociated cells, microscopy, radiography, scintillation counting, etc. Any suitable alternative methods can of qualitative or quantitative detection of levels or amounts of differentially expressed polypeptide can be used, for example ELISA, western blot, immunoprecipitation, radio-immunoassay, etc.

Conditioned medium, i.e. medium in which cells of the invention have been grown for a period of time sufficient to allow secretion of soluble factors into the culture, may be isolated at various stages and the components analyzed for the presence of factors secreted by the cells. Separation can be achieved with HPLC, reversed phase-HPLC, gel electrophoresis, isoelectric focusing, dialysis, or other non-degradative techniques, which allow for separation by molecular weight, molecular volume, charge, combinations thereof, or the like. One or more of these techniques may be combined to enrich further for specific fractions.

Where an animal is being tested, the severity of skin inflammation may be assessed. For example, the severity of psoriasis is measured by the Psoriasis Area Severity Index (PASI) (see e.g., Fleischer et al. (1999), J. Dermatol. 26:210-215 and Tanew et al. (1999), Arch Dermatol. 135:519-524) or various psoriasis global assessment scores such as Physician's Global Assessment (PGA) which are well-known to those skilled in the art of clinical trials for psoriasis. Typically, in a clinical trial (e.g., a phase II or phase III trial), the improvement in PASI or score in the patients treated with a candidate agent, relative to the control group of patients receiving no treatment or placebo or another agent, will be statistically significant, for example at the p=0.05 or 0.01 or even 0.001 level.

Formulations

Therapeutic agents, i.e. agents that act on Ras signaling pathways, as described above can be incorporated into a variety of formulations for therapeutic administration by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intrathecal, nasal, intracheal, etc., administration. The active agent may be systemic after administration or may be localized by the use of regional administration, intramural administration, or use of an implant that acts to retain the active dose at the site of implantation.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The effective amount of a therapeutic composition to be given to a particular patient will depend on a variety of factors, several of which will be different from patient to patient. A competent clinician will be able to determine an effective amount of a therapeutic agent to administer to a patient. Dosage of the agent will depend on the treatment, route of administration, the nature of the therapeutics, sensitivity of the patient to the therapeutics, etc. Utilizing $LD_{50}$ animal data, and other information, a clinician can determine the maximum safe dose for an individual, depending on the route of administration. Utilizing ordinary skill, the competent clinician will be able to optimize the dosage of a particular therapeutic composition in the course of routine clinical trials. The compositions can be administered to the subject in a series of more than one administration. For therapeutic compositions, regular periodic administration will sometimes be required, or may be desirable. Therapeutic regimens will vary with the agent, e.g. an NSAID such as indomethacin may be taken for extended periods of time on a daily or semi-daily basis, while more selective agents may be administered for more defined time courses, e.g. one, two three or more days, one or more weeks, one or more months, etc., taken daily, semi-daily, semi-weekly, weekly, etc.

A pharmaceutically or therapeutically effective amount of the composition is delivered to the subject. The precise effective amount will vary from subject to subject and will depend upon the species, age, the subject's size and health, the nature and extent of the condition being treated, recommendations of the treating physician, and the therapeutics or combination of therapeutics selected for administration. Thus, the effective amount for a given situation can be determined by routine experimentation. For purposes of the present invention, generally a therapeutic amount may be in the range of about 0.001 mg/kg to about 100 mg/kg body weight, in at least one dose. The subject may be administered in as many doses as is required to reduce and/or alleviate the signs, symptoms, or causes of the disorder in question, or bring about any other desired alteration of a biological system.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

Allergic and Inflammatory Disorders

The animals and cells of the invention may be used in screening agents and therapies for inflammatory disorders, particularly those having an allergic, or IgE mediated component, or a T cell-mediated component. Anaphylactic allergens are those antigens that pose a risk of anaphylactic reaction in hypersensitive individuals. Anaphylaxis is an acute, systemic allergic reaction that occurs after an individual has become sensitized to an antigen. Anaphylaxis is associated with the production of high levels of IgE antibodies and with the release of histamines, which cause muscle contractions, constriction of the airways, and dilation of blood vessels. Symptoms of anaphylactic reactions include hives, generalized itching, nasal congestion, wheezing, difficulty breathing, cough, cyanosis, lightheadedness, dizziness, confusion, slurred speech, rapid pulse, palpitations, nausea and vomiting, abdominal pain or cramping, skin redness or inflammation, nasal flaring, intercostal retractions, etc.

Allergy, or atopy is an increased tendency to IgE-based sensitivity resulting in production of specific IgE antibody to an immunogen including, for example, insect venom, dust mites, pollens, molds, animal dander, food antigens, or latex. Allergic responses are antigen specific. Atopic disease is manifested by allergic inflammation in the respiratory tract, skin or gastrointestinal tract, as well as by elevated serum IgE, eosinophilia and the symptoms of wheezing, sneezing or hives. In addition, allergic inflammatory responses are characterized by the presence of Th2 lymphocytes producing high levels of IL-4, IL-5, IL-9 and IL-13, which enhance the growth, differentiation and/or recruitment of eosinophils, mast cells, basophils and B cells producing IgE.

Allergens are immunogenic compounds that cause Th2-type T cell responses and IgE B cell responses in susceptible individuals. Allergens include antigens found in foods such as fruits (e.g., melons, strawberries, pineapple and other tropical fruits), peanuts, peanut oil, other nuts, milk proteins, egg whites, shellfish, tomatoes, etc.; airborne antigens such as grass pollens, animal danders, house mite feces, etc.; drug antigens such as penicillins and related antibiotics, sulfa drugs, barbituates, anticonvulsants, insulin preparations (particularly from animal sources of insulin), local anesthetics (e.g., Novocain), and iodine (found in many X-ray contrast dyes); insect venoms and agents responsible for allergic dermatitis caused by blood sucking arthropods such as *Diptera*, including mosquitos (*Anopheles* sp., *Aedes* sp., *Culiseta* sp., *Culex* sp.), flies (*Phlebotomus* sp., *Culicoides* sp.) particularly black flies, deer flies and biting midges, ticks (*Dermmacenter* sp., *Ornithodoros* sp., *Otobius* sp.), fleas (e.g., the order *Siphonaptera*, including the genera *Xenopsylla, Pulex* and *Ctenocephalides felis felis*); and latex. The specific allergen may be any type of chemical compound such as, for example, a polysaccharide, a fatty acid moiety, a protein, etc. Antigen preparations may be prepared by any available technique including, for example, isolation from natural sources, in vivo or in vitro expression of recombinant DNA molecules (see, for example, Zeiler et al. (1997) *J. Allergy Clin. Immunol.* 100(6 Pt 1):721-727, chemical synthesis, or other technique known in the art.

The transgenic animals and cells of the invention are particularly useful in screening assays and models for atopic dermatitis, which is a chronic, pruritic, superficial inflammation of the skin, frequently associated with a personal or family history of allergic disorders. The disorder is triggered by various environmental agents and factors. Patients with atopic dermatitis usually have high serum levels of reaginic (IgE) antibodies, peripheral eosinophilia, and high levels of cAMP phosphodiesterase in their WBCs.

Atopic dermatitis may begin in the first few months of life, with red, weeping, crusted lesions on the face, scalp, diaper area, and extremities. In older children or adults, it may be more localized and chronic, typically appearing as erythema and lichenification in the antecubital and popliteal fossae and on the eyelids, neck, and wrists. The course is unpredictable. Although the dermatitis often improves by age 3 or 4 yr, exacerbations are common during childhood, adolescence, or adulthood. The dermatitis may become generalized. Secondary bacterial infections and regional lymphadenitis are common. Frequent use of proprietary or prescribed drugs exposes the patient to many topical allergens, and contact dermatitis may aggravate and complicate atopic dermatitis, as may the generally dry skin that is common in these patients. Intolerance to primary environmental irritants is common, and emotional stress, ambient temperature or humidity changes, bacterial skin infections, fragrances, fabric softeners, and wool garments commonly cause exacerbations.

Patients with long-standing atopic dermatitis may develop cataracts while in their 20s or 30s. Cataracts may be a feature of atopy or may result from extensive systemic and topical corticosteroid use. Herpes simplex may induce a generalized painful vesicular eruption and sometimes a grave febrile illness (eczema herpeticum) in atopic patients. Diagnosis is based on the distribution and duration of lesions and often on a family history of atopic disorders and the presence of lichenification.

Corticosteroid creams or ointments applied three times daily are often prescribed. Older adults may benefit from treatment with ultraviolet radiation B, psoralen plus high-intensity ultraviolet A, or narrow band ultraviolet A without psoralen. Oral corticosteroids may help reduce side effects. The initial dose should be continued for several weeks, then slowly decreased while the patient starts using topical drugs. For unusually widespread, recalcitrant, or disabling cases, experimental treatments, such as oral emulsified cyclosporine 1.5 to 2.5 mg/kg bid in adults, have proven useful. Tacrolimus is a topical immunosuppressive ointment, which may be useful in children and adults with severe atopic dermatitis. Newly developed phosphodiesterase-4 inhibitors may become important therapy.

Psoriasis is a chronic skin disease, characterized by scaling and inflammation. Psoriasis affects 1.5 to 2 percent of the United States population, or almost 5 million people. It occurs in all age groups and about equally in men and women. People with psoriasis suffer discomfort, restricted motion of joints, and emotional distress. When psoriasis develops, patches of skin thicken, redden, and become covered with silvery scales, referred to as plaques. Psoriasis most often occurs on the elbows, knees, scalp, lower back, face, palms, and soles of the feet. The disease also may affect the fingernails, toenails, and the soft tissues inside the mouth and genitalia. About 10 percent of people with psoriasis have joint inflammation that produces symptoms of arthritis. The chronic skin inflammation of psoriasis is associated with hyperplastic epidermal keratinocytes and infiltrating mononuclear cells, including CD4+ memory T cells, mast cells, neutrophils and macrophages.

It must be noted that as used herein and in the appended claims, the singular forms "a", "and", and "the" include plural referents unless the context clearly dictates otherwise. Thus, for example, reference to "a construct" includes a plurality of such constructs and reference to "the RabGEF1-encoding nucleic acid" includes reference to one or more RabGEF1-encoding nucleic acids and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

It is to be understood that this invention is not limited to the particular methodology, protocols, cell lines, animal species or genera, constructs, and reagents described, as such may vary. It is also to be understood that the terminology used herein is for the purpose of describing particular embodiments only, and is not intended to limit the scope of the present invention, which will be limited only by the appended claims.

EXAMPLE 1

RabGEF1 is a Negative Regulator of Mast Cell Activation and Skin Inflammation

RabGEF1 is a regulator of FcεRI-dependent and Ras-mediated signaling and functional responses in mast cells. RabGEF1 is a Rab5 binding protein that exhibits GEF activity for Rab5 in vitro. Rab5 is activated by complex formation between RabGEF1 and Rabaptin-5, an effector of Rab5. In vitro, RabGEF1 binds to Ras and negatively regulates Ras activation, the activation of Ras-dependent signaling pathways and the secretion of mediators and cytokines in mast cells activated by FcεRI aggregation. Moreover, in response to FcεRI aggregation, mast cells derived from Rabgef1 knockout mice exhibit enhanced activation of Ras-mediated signaling pathways, as well as enhanced levels of degranulation and release of mediators and cytokines. Rabgef1$^{-/-}$ mice develop severe skin inflammation and exhibit elevated numbers of skin mast cells, as well as increased serum levels of IgE and histamine.

Figure 1A:
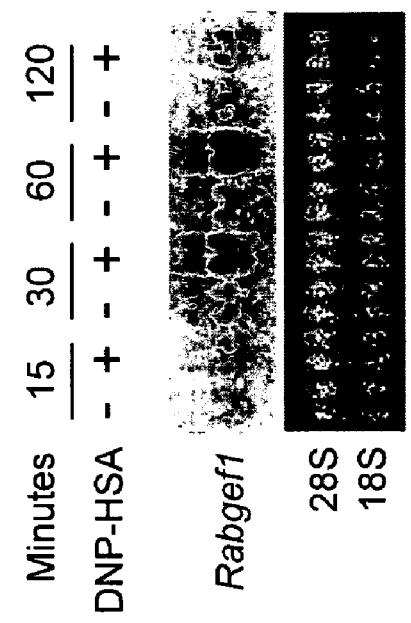

Expression of RabGEF1 in mast cells activated via FcεRI. Differential display was used to isolate genes that were differentially regulated after FcεRI-dependent activation in the mouse mast cell line, CI.MC/C57.1. A differentially expressed band (60-4) was identified. In Northern blot analysis, the 60-4 probe hybridized to a mRNA transcript whose expression was rapidly up-regulated in CI.MC/C57.1 cells and in primary populations of mouse bone marrow-derived cultured mast cells (BMCMCs) that had been stimulated through the FcεRI for 30 min and 1 hour, but returned to ~ baseline levels after 2 hours (FIG. 1a). Using the 60-4 probe to screen mouse cDNA libraries, we found that the deduced amino acid sequence of the full-length cDNA clone obtained was virtually identical to that of bovine Rabex-5, a Rab5 binding protein that exhibits in vitro GEF activity. Rabex-5 has recently been designated as RabGEF1 by the Mouse Genome Database of the Mouse Genome Informatics (MGI).

Western blot analysis using an antibody against mouse RabGEF1 showed that levels of RabGEF1 protein in both CI.MC/C57.1 mast cells and BMCMCs were decreased by 1 hour after FcεRI-dependent stimulation, were even lower by 2 hours, and returned to normal by ~6 hours (FIG. 1b), perhaps reflecting the up-regulation of Rabgef1 mRNA expression that occurs in association with the initial phase of cell activation (FIG. 1a).

RabGEF1 binds to Ras. Over amino acid residues 227-380, mouse RabGEF1 shares significant sequence homology in the Vps9p domain with members of a novel Rab5 binding protein family that includes Vps9p, RIN1 and JC265 (RIN2) (FIG. 2a). Vps9p is the GEF for the Rab5 ortholog Vps21p in yeast and both RIN1 and JC265 exhibit GEF activity for Rab5. However, mammalian RIN1 and JC265 were initially identified as inhibitors of an activated RAS2 allele in S. cerevisiae. Within the Vps9p domain, three GTPase binding homology (GBH) motifs have been proposed. The mouse RabGEF1 contains an amino acid sequence (SEQ ID NO:5, residues 85-93; SADDFLPTL) that matches well with the proposed GBH motif II (SEQ ID NO:10; GADXFLPVL). Moreover, the GBH motif II is located in a region of JC265 and RIN1 that shares significant homology with several rasGAP-like proteins such as human rasGAP, yeast IRA1 and IRA2, neurofibromin and sarl.

We assessed whether RabGEF1 also can bind directly to Ras and/or influence Ras activation. Using the yeast two-hybrid system, we found that mouse RabGEF1 can interact physically with wild-type mouse H-Ras (FIG. 2b). In a β-galactosidase assay, the strongest positive interactions were detected for full-length mouse RabGEF1 and the C-terminal region of the protein, whereas weaker interactions were detected for the N-terminal region and the Vps9p domain. Thus, in both RabGEF1 and RIN1, the C-terminal portion of the protein, that is 3' distal to the Vps9p domain, contributes to the molecule's Ras binding activity. However, unlike RIN1, mouse RabGEF1 did not appear to bind to yeast Ras2p (FIG. 2b).

Figure 2C:
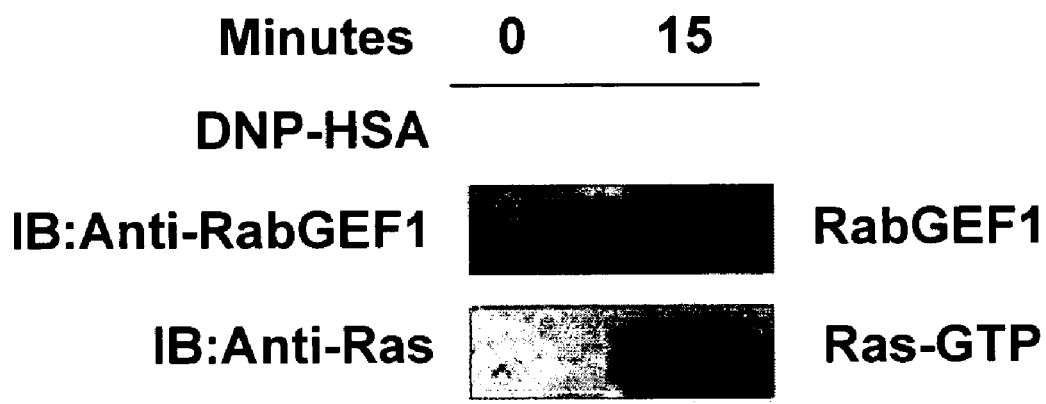

To assess whether RabGEF1 can also bind to activated Ras during physiological cell activation, we used the Ras-binding domain (RBD) of Raf1 to pull-down Ras-GTP from lysates of CI.MC/C57.1 mast cells that were stimulated with IgE and antigen via FcεRI and probed the immunoprecipitate with an antibody to mouse RabGEF1. The presence of RabGEF1 protein was detected in the immunoprecipitate containing activated Ras-GTP (FIG. 2c). These data thus indicate that RabGEF1 can bind to the activated form of Ras in mast cells activated in response to FcεRI aggregation.

RabGEF1 is a negative regulator of Ras-mediated signaling and functional responses in mast cells in vitro. To test the hypothesis that RabGEF1 may function as a negative regulator of Ras-mediated signaling and functional responses during cell activation, we over-expressed a mouse Rabgef1 antisense construct in CI.MC/C57.1 mast cells. While over-expression of the antisense construct did not appear to affect the basal levels of RabGEF1 protein expression in these cells, it did inhibit the replenishment of RabGEF1 protein at 4 to 6 hours after FcεRI-dependent cell activation, resulting in a sustained and prolonged reduction in RabGEF1 protein levels (FIG. 3a).

FcεRI aggregation was associated with the rapid activation of Ras in control transfected mast cells 15 min after stimulation, which declined to basal levels by ~1 hour; Rabgef1 antisense transfected mast cells exhibited a higher basal level of Ras activity, higher levels of Ras activation after stimulation, and a more sustained response (FIG. 3b). Similarly, levels of activation of ERK, the downstream effector of the Ras/Raf/MEK cascade, were significantly potentiated in the antisense transfectants at 30 min and 1 hour after stimulation (FIG. 3c). These data are thus consistent with the hypothesis that decreased expression of RabGEF1 can potentiate Ras activation and Ras-mediated signaling responses elicited by FcεRI aggregation.

In addition to Ras-mediated activation of ERK, Rac and Cdc42, members of the Rho family of GTPases, have been shown to enhance ERK activity through the activation of their effector p21-activated kinase (Pak). Rac and Cdc42 can potentiate ERK activation by synergizing with Raf-1 through mechanisms that involve phosphorylation of MEK1 by Pak1 on Thr292 and Ser298, which is required for interaction with Raf-1, and phosphorylation of Raf-1 on Ser338 by Pak3. However, we found that both the antisense and the control transfectants exhibited similar levels of activation of C-Jun N-terminal kinase (JNK) after FcεRI aggregation (FIG. 3d). Since JNK is the key downstream effector of the Rac(Cdc42)/Pak/MEKK1/SEK1 cascade, our data suggest that RabGEF1 does not significantly suppress the activities of Rac and Cdc42 during FcεRI-dependent mast cell activation.

Figure 4C:
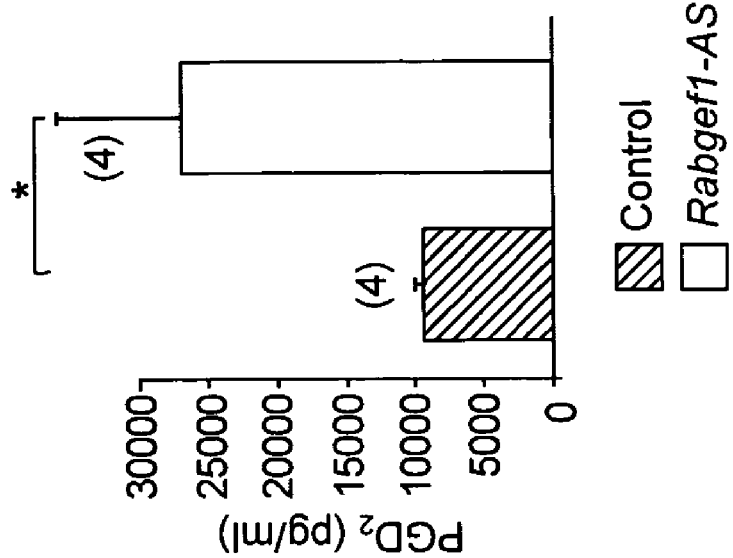
FIG. 4A-4C. Potentiation of cytokine release in CI.MC/C57.1 mast cells transfected with the Rabgef1 antisense expression vector in response to FcεRI-dependent cell activation. (a) Release of β-hexosaminidase (β-Hex) induced by FcεRI aggregation from CI.MC/C57.1 mast cells transfected with the antisense expression vector (Rabgef1-AS) or the control CMV vector (Control). Transfectant cells sensitized with anti-DNP IgE mAb for 2 hours were challenged with DNP-HSA (100 ng/ml). Specific release of β-Hex (background release was ≦6%) was measured one hour after antigen challenge. (b) Release of IL-6 induced by FcεRI aggregation from Rabgef1-AS or Control transfectants. IL-6 release was measured by ELISA assay 6 hours after antigen challenge as in (a). (c) Release of $PGD_2$ induced by FcεRI aggregation from Rabgef1-AS or Control transfectants. $PGD_2$ release was measured by an enzyme immunoassay one hour after antigen challenge as in (a). The numbers over the columns illustrated in (a), (b) and (c) indicate the number of stable lines of transfectants established from two independent transfections and assayed in this study. *$p<0.05$ vs Control by unpaired Student's t test.
Figure 4B:
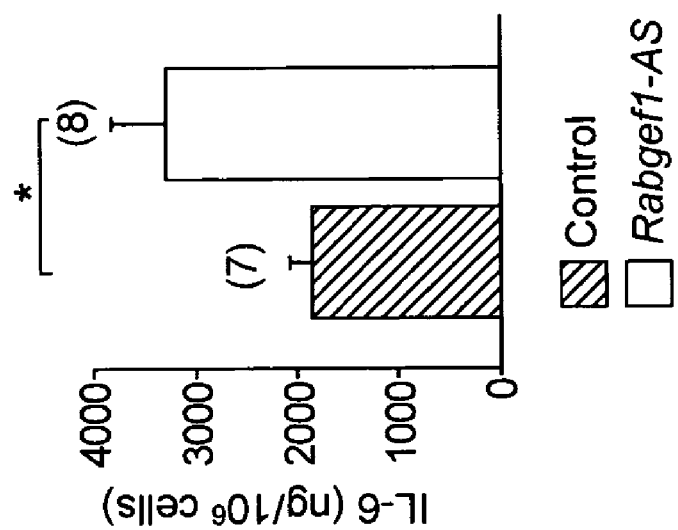

We next investigated whether knocked-down expression of RabGEF1 could lead to changes in functional responses induced by FcεRI aggregation in mast cells. From two independent transfections, we established eight stable lines of Rabgef1 antisense transfectants and seven stable lines of control CMV vector transfectants. While there were no significant differences between the amounts of a representative pre-formed mediator, β-hexosaminidase (β-Hex), released from the antisense or control transfectant groups in response to FcεRI aggregation under the conditions tested (FIG. 4a), the release of interleukin-6 (IL-6) was significantly enhanced (by a mean value of ~70%) in the antisense group (FIG. 4b). In general, those antisense transfectants that exhibited the largest and most sustained reduction in RabGEF1 protein levels after FcεRI aggregation also exhibited the greatest enhancement of IL-6 release; similar findings were obtained when we assessed release of tumor necrosis factor-α (TNF-α) (data not shown). The release of $PGD_2$ from the antisense transfectants upon FcεRI aggregation was also significantly enhanced (FIG. 4c).

Generation of Rabgef1$^{-/-}$ mice. Even though Rabgef1 antisense transfectants secreted increased levels of cytokines and $PGD_2$ in response to IgE- and antigen than did control transfectants (FIG. 4), the antisense transfectants expressed apparently normal levels of RabGEF1 at baseline and continued to express detectable levels of the protein (albeit markedly reduced compared to those in control transfectants) after FcεRI-dependent stimulation (FIG. 3a). To assess the effects on mast cell function of a complete lack of RabGEF1, we generated Rabgef1 knockout mice (FIGS. 5a, b).

Many Rabgef1$^{-/-}$ pups died during the first week of life, and only a few survived into adulthood. Western blot analysis of BMCMCs generated from Rabgef1$^{-/-}$ and Rabgef1$^{+/-}$ mice and age-matched wild-type littermates showed that the expression of the full-length 57 kDa RabGEF1 protein was undetectable in Rabgef1$^{-/-}$ BMCMCs and was reduced in Rabgef1$^{\pm}$ BMCMCs (FIG. 5c). Moreover, no expression of any truncated RabGEF1 protein products could be detected in BMCMCs derived from Rabgef1$^{-/-}$ or Rabgef1$^{\pm}$ mice.

Figure 6B:
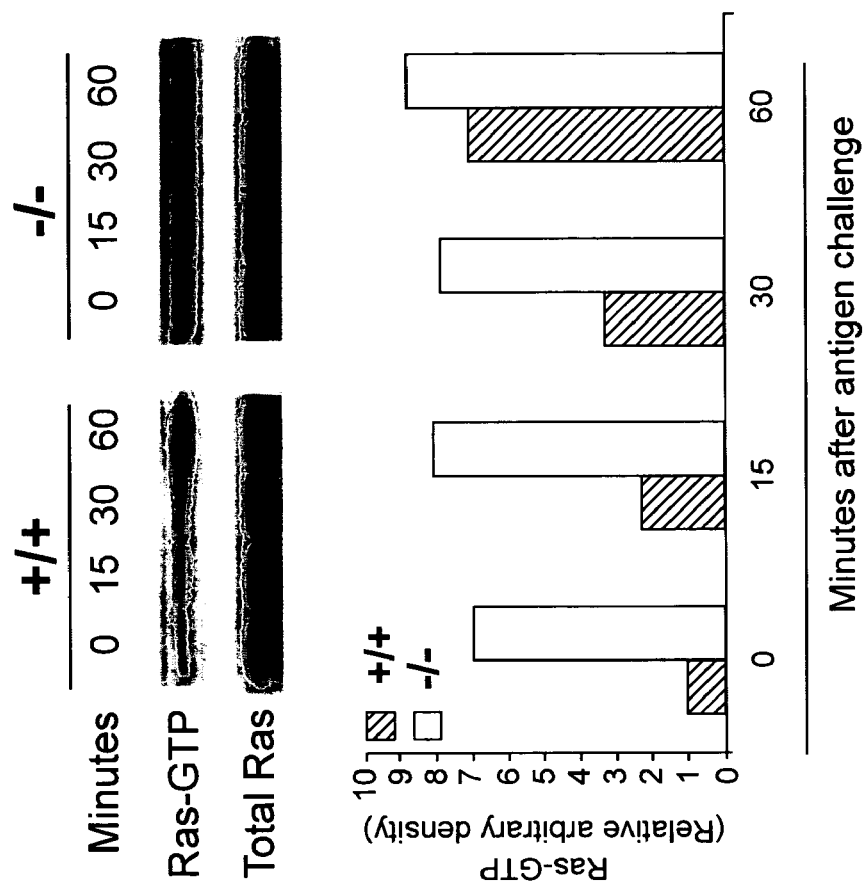
FIG. 6A-6F. Potentiation of Ras-mediated signaling responses in $Rabgef1^{-/-}$ BMCMCs in response to FcεRI-dependent cell activation. (a) Flow cytometry analysis of expression of FcεRI receptors in $Rabgef1^{-/-}$ (−/−) and wild-type (+/+) BMCMCs that had been cultured for 10 weeks. (b) Kinetics of Ras activation induced by FcεRI aggregation in $Rabgef1^{-/-}$ (−/31 ) vs. wild-type (+/+) BMCMCs. Cells were sensitized with anti-DNP IgE mAb overnight and then challenged with DNP-HSA (10 ng/ml). (c) Kinetics of ERK activation induced by FcεRI aggregation, as in (b), in $Rabgef1^{-/-}$ (−/−) vs. wild-type (+/+) BMCMCs. (d) Kinetics of JNK activation induced by FcεRI aggregation, as in (b), in $Rabgef1^{-/-}$ (−/−) vs. wild-type (+/+) BMCMCs. (e) Kinetics of Rac1 activation induced by FcεRI aggregation, as in (b), in $Rabgef1^{-/-}$ (−/−) vs. wild-type (+/+) BMCMCs. Active Rac1 was immunoprecipitated using GST-fusion protein containing p21-binding domain (PBD) of Pak1, and the pulled-down Rac1-GTP was detected using an anti-Rac1 antibody. (f) Kinetics of Cdc42 activation induced by FcεRI aggregation, as in (b), in $Rabgef1^{-/-}$ (−/−) vs. wild-type (+/+) BMCMCs. Active Cdc42 was immunoprecipitated using GST-fusion protein containing PBD of Pak1, and the pulled-down Cdc42-GTP was detected using an anti-Cdc42 antibody. Findings illustrated in (b)-(f) are representative of those obtained with 3-4 separate determinations, all of which gave similar results. All signals were quantified by densitometric scanning.
Figure 6A:
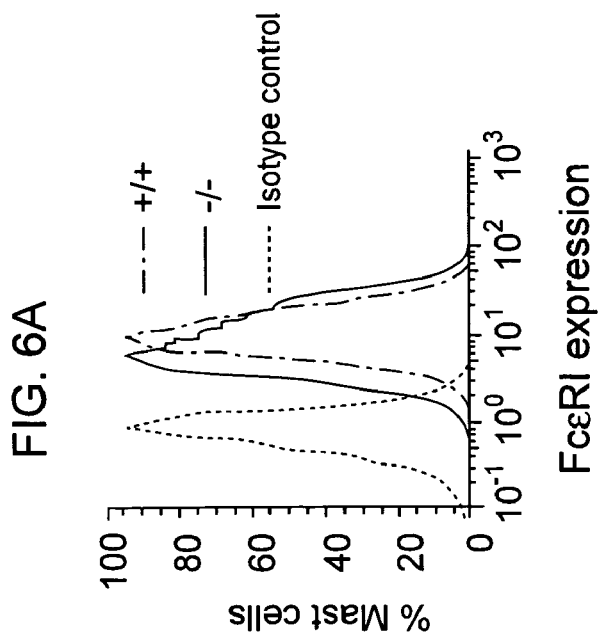
Figure 6C:
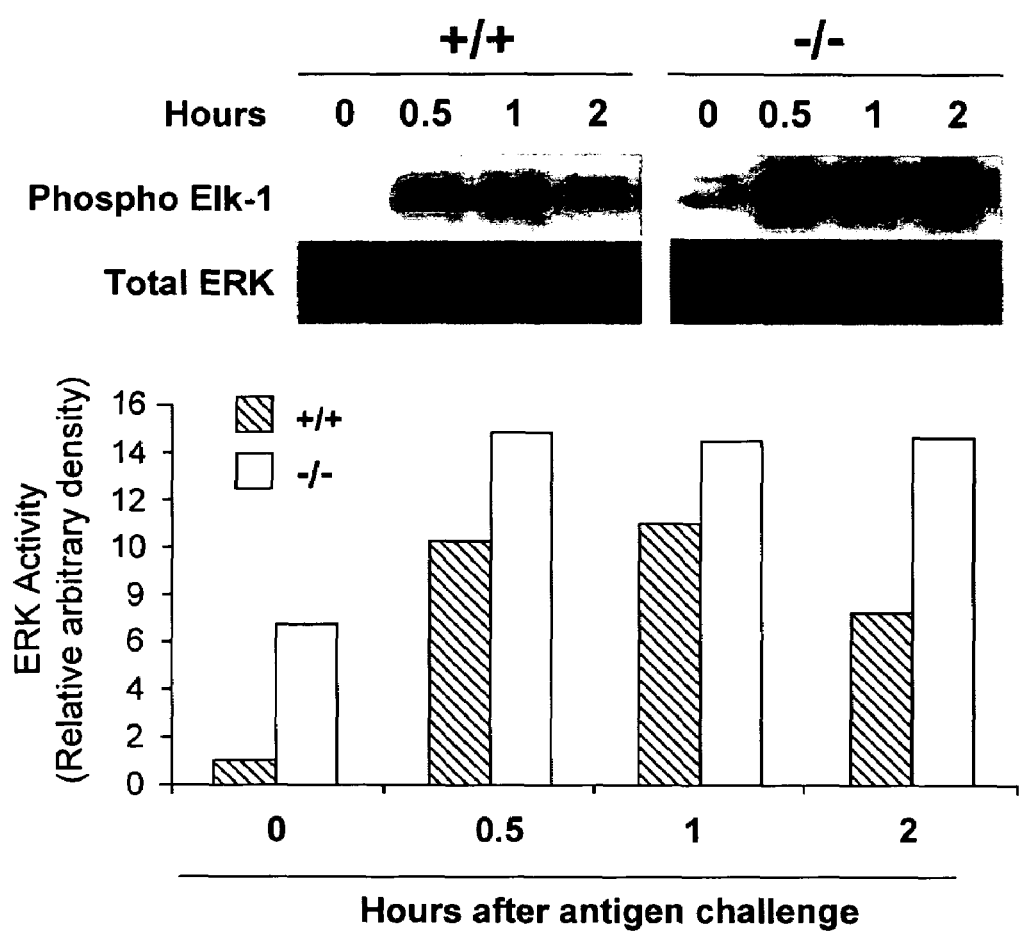

Enhanced FcεRI-dependent Ras signaling responses in Rabgef1$^{-/-}$ mast cells. By flow cytometry, BMCMCs derived from Rabgef1$^{-/-}$ mice expressed slightly lower levels of FcεRI (FIG. 6a). However, Rabgef1$^{-/-}$ BMCMCs exhibited higher levels of Ras activation, both at baseline and after stimulation with IgE and antigen (FIG. 6b). The very high basal levels of Ras activation found in the Rabgef1$^{-/-}$ BMCMCs are reminiscent of a similar effect that was observed with BMCMCs deficient in neurofibromin, which functions as a rasGAP protein and a negative effector of Ras. Furthermore, Rabgef1$^{-/-}$ BMCMCs exhibited higher than wild-type levels of ERK activation at baseline and at 0.5, 1 and 2 hours after stimulation with antigen (FIG. 6c). High levels of ERK activation were sustained longer after stimulation than in the wild-type cells (FIG. 6c). Taken together, these results are consistent with the observations in our Rabgef1 knock-down studies, indicating that RabGEF1 functions as a significant negative regulator of Ras signaling.

Figure 6D:
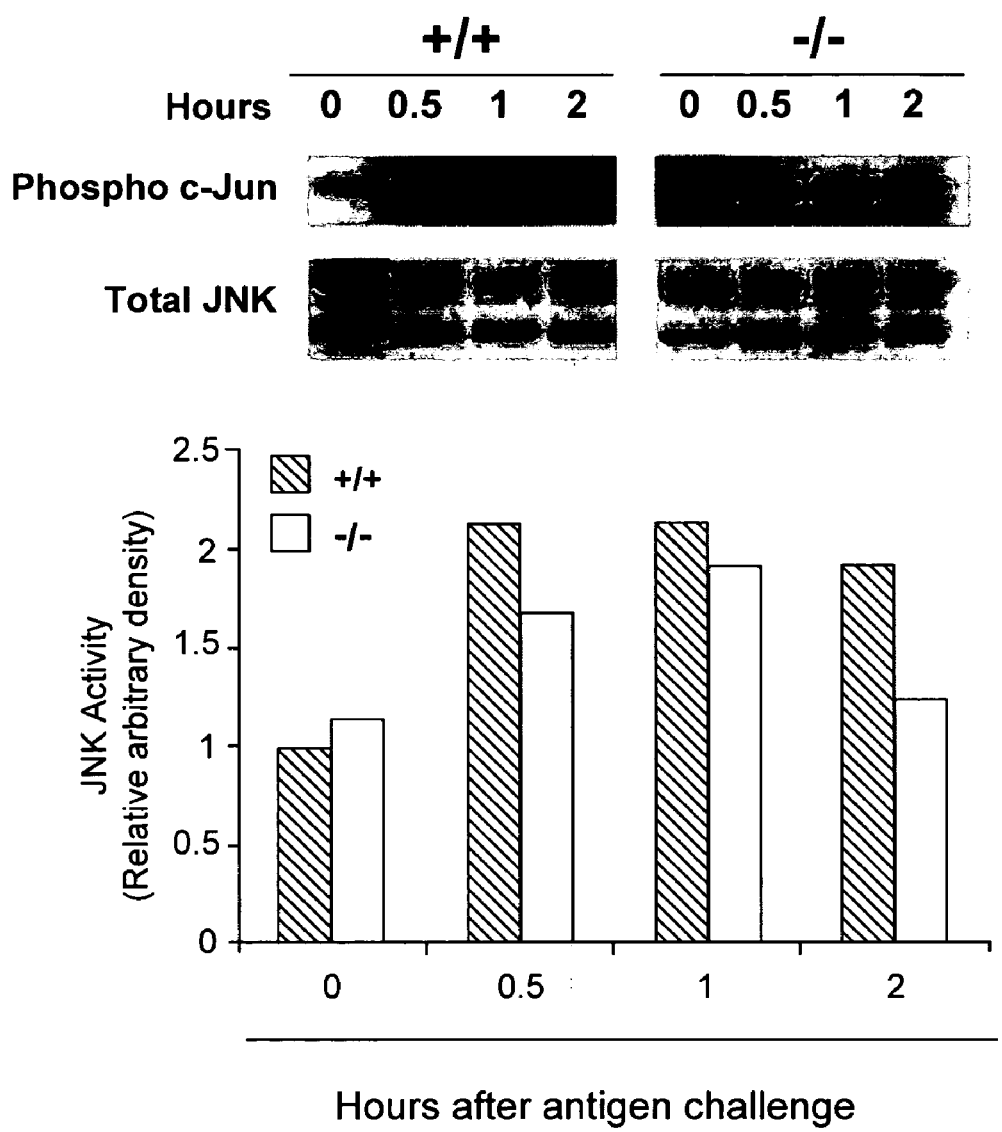
Figure 6E:
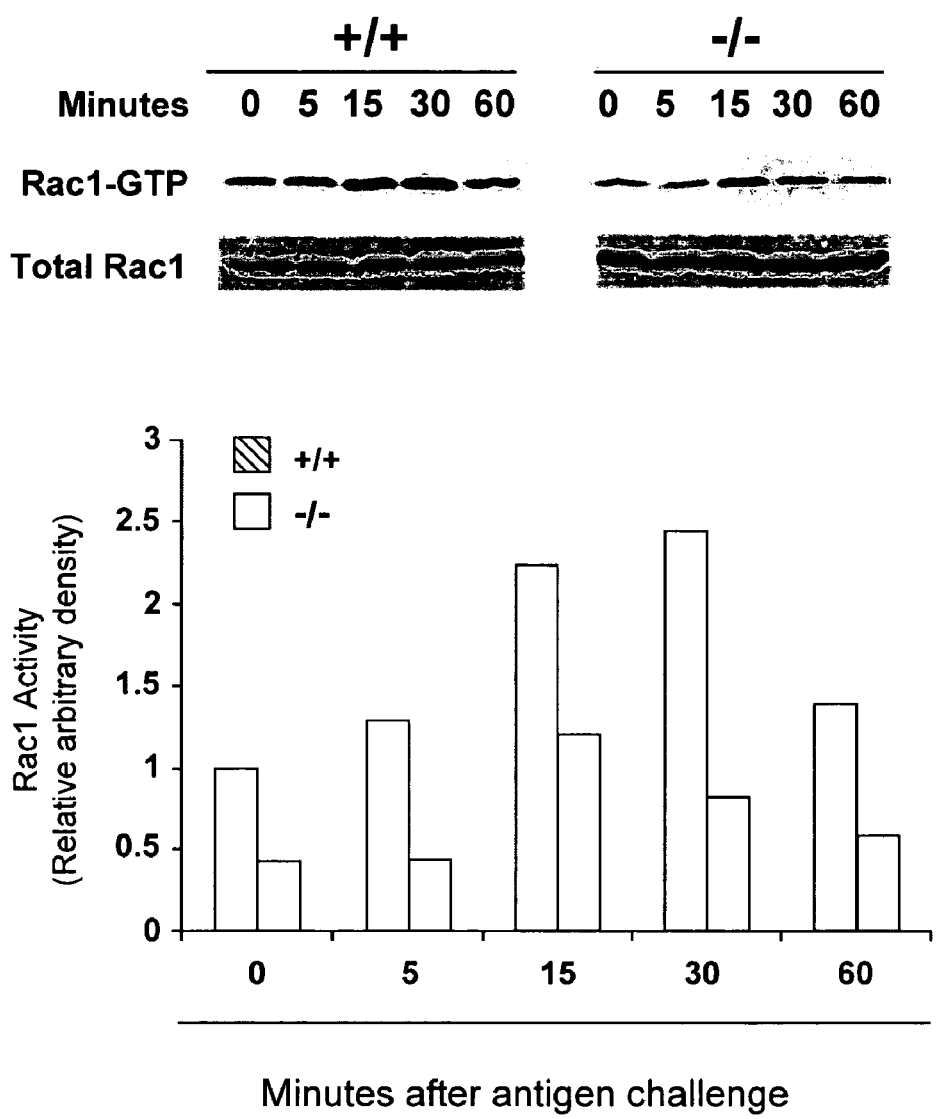
Figure 6F:
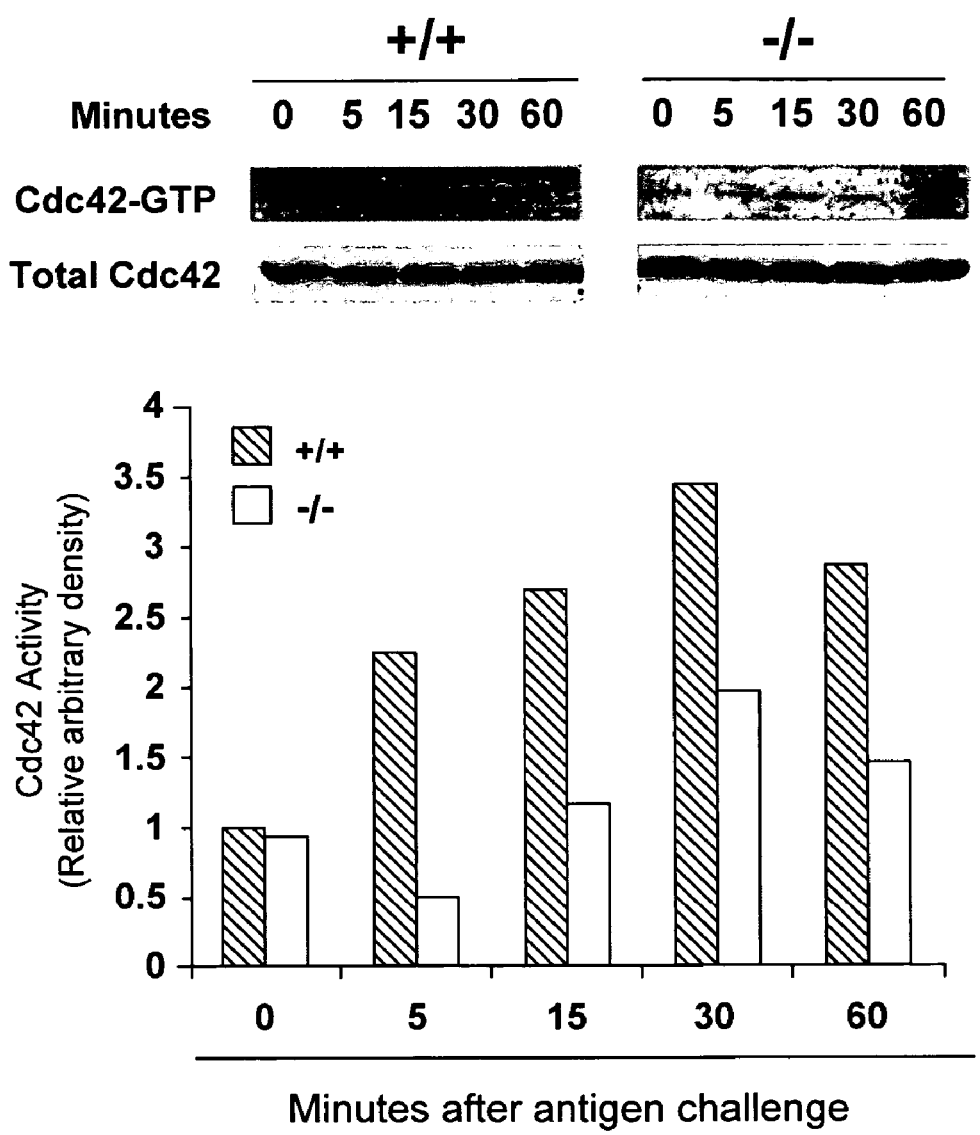

Moreover, we found that JNK activation after FcεRI aggregation was not potentiated in Rabgef1$^{-/-}$ BMCMCs as compared with the wild-type cells (FIG. 6d), consistent with the findings obtained in our knock-down studies (FIG. 3d). Indeed, the activation of Rac1 and Cdc42, the upstream effectors of JNK, were down-regulated in the Rabgef1$^{-/-}$ cells after antigen stimulation (FIGS. 6e, f). These data thus support the conclusion that the negative regulatory effects of RabGEF1 on GTP loading in response to FcεRI aggregation are specific for Ras-GTPase, but not for the Rho family of GTPases such as Rac or Cdc42.

Figure 4A:
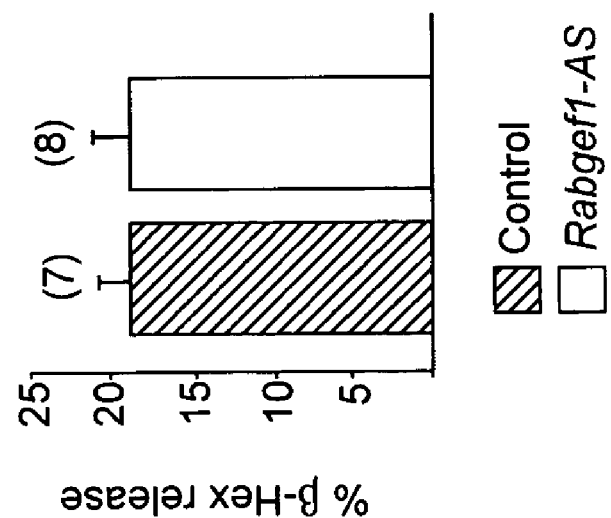

Enhanced FcεRI-dependent functional responses in Rabgef1$^{-/-}$ mast cells. As shown in FIG. 7a, significant enhancement of the release of the pre-formed mediator, β-Hex, in response to IgE and antigen was observed in Rabgef1$^{-/-}$ BMCMCs at all concentrations of DNP-HSA≧10 ng/ml. These results thus differ from those obtained in the Rabgef1 knock-down studies, in which it was found that a reduced expression of RabGEF1 had no significant effect on β-Hex release when the cells were challenged with DNP-HSA at the one concentration tested (100 ng/ml) (FIG. 4a).

In accord with our observations in the knock-down studies, Rabgef1$^{-/-}$ BMCMCs released amounts of $PGD_2$ and $LTC_4$, and cytokines (IL-6 and TNF-α), in response to FcεRI aggregation that were significantly higher than those of Rabgef1$^{+/+}$ BMCMCs at all concentrations of antigen tested (FIG. 7b-e). These data are thus consistent with the view that the Ras/Raf/MEK/ERK cascade represents a major signaling pathway for the synthesis and release of lipid mediators and cytokines in mast cells. However, the findings in FIG. 7a implicate RabGEF1 as a significant negative regulator of degranulation and the release of granule-associated mediators in mast cells as well.

Rabgef1$^{-/-}$ mice develop severe skin inflammation. All Rabgef1$^{-/-}$ mice that survived to adulthood developed severe skin inflammation. The onset of skin lesions was variable; grossly detectable lesions usually first appeared at 6-8 weeks. However, the lesions were detectable microscopically in Rabgef1$^{-/-}$ mice as young as 3-4 weeks old. Grossly, the skin lesions were characterized as raised, white plaque-like scales affecting the ear pinnas and periocular skin (associated with facial alopecia), which eventually spread to involve skin of the cervical area and dorsum. Multiple microbiological cultures from skin lesions were negative for common skin pathogens.

Figure 8A:
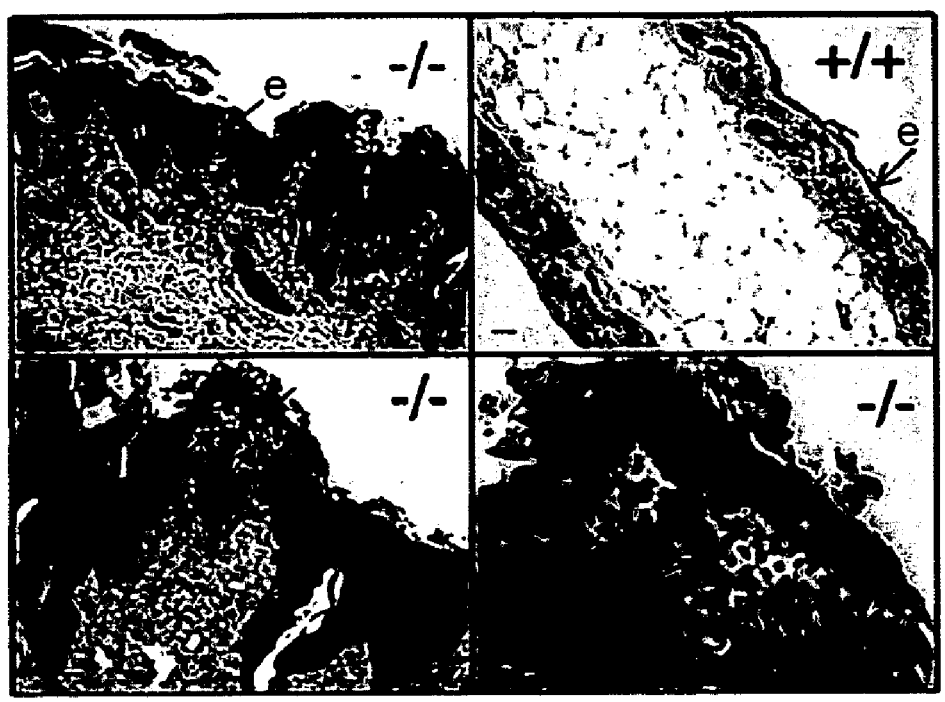

Histologically, the skin lesions exhibited epidermal hyperplasia, with hyperkeratosis and prominent dermal inflammation accompanied by increased vascularity; in severe lesions, there were foci of intracellular edema in the epidermis (i.e., spongiosis), and epidermal microabscesses, consisting of neutrophil accumulation within the superficial layer of the epidermis (FIG. 8a). Dense infiltrates of lymphocytes, eosinophils and monocytes/macrophages, as well as mast cells, were present in the dermis. Furthermore, many Rabgef1$^{-/-}$ mice exhibited serum levels of IgE (FIG. 8b) and histamine (FIG. 8c) that were much higher than those in age-matched wild-type animals.

The skin of Rabgef1$^{-/-}$ mice exhibits increased numbers of mast cells and histological evidence of mast cell degranulation. The skin of Rabgef1$^{-/-}$ mice contained significantly more mast cells than in wild-type mice (FIGS. 8d, 8e). The difference was apparent in mice as young as 1-week old, even before the mice developed obvious skin lesions (mast cells/mm$^2$ of dermis: +/+=39.7±5.5[n=5], −/−=89.4±11.7 [n=3]; p<0.01). In older Rabgef1$^{-/-}$ mice, mast cell numbers were strikingly higher at sites exhibiting severe inflammation than in less severely affected skin (FIG. 8d), and some mast cells exhibited histological evidence of degranulation (FIG. 8e).

Here we show that RabGEF1 can physically interact with Ras and function as a negative regulator of Ras activation and Ras-associated downstream signaling and functional responses during FcεRI-dependent mast cell activation. The negative regulatory effects of RabGEF1 appear to be specific for those cellular responses that are mediated through the activation of Ras-GTPase, in that both our antisense experiments and studies in Rabgef1$^{-/-}$ mast cells indicate that RabGEF1 does not represent a negative regulator of the activation of other small GTPases, such as Rac or Cdc42. The physiological importance of RabGEF1 as a negative regulator of IgE- and antigen-dependent mast cell activation is shown clearly by the phenotype of Rabgef1$^{-/-}$ mast cells: these cells release significantly more mediators and cytokines in response to challenge with IgE and antigen than do mast cells derived from the wild-type mice.

RabGEF1 was first identified as a binding protein and GEF for Rab5, a small GTPase involved in early endosomal trafficking and endocytosis. However, RabGEF1 shares significant homology in the Vps9p domain with mammalian RIN1, a negative Ras effector. RIN1 has recently also been shown to exhibit GEF activity for Rab5 through its consensus Vps9p domain, and such GEF activity is enhanced when the Ras association domain of RIN1 is occupied by activated Ras. RIN1 can also stimulate endosome fusion and receptor-mediated endocytosis, a finding that supports other evidence indicating that important functional links exist between endocytosis and signaling. Indeed, RabGEF1, together with PKB/Akt, p120 GAP and RIN1, appear to represent a class of Ras-dependent and Rab-associated regulatory proteins that function, in part, to integrate signal transduction and endocytosis.

Although RabGEF1 and RIN1 share homology in the Vps9p domain, and can function in vitro as both GEF proteins for Rab5 and Ras binding proteins, the cellular responses that are mediated by the two proteins appear to be distinct. While expression of RIN1 can inhibit Ras activation in a fibroblast transformation assay, the N-terminal portion of RIN1 can enhance, rather than inhibit, cellular transformation induced by BCR-ABL1. By contrast, RabGEF1 can negatively regulate all Ras-mediated signaling and functional responses we have examined. Furthermore, although both Rabgef1 and Rin1 exhibit a very wide pattern of gene expression in various tissues, the mouse phenotypes resulting from the targeted deletion of these proteins are quite different. Rin1$^{-/-}$ mice have not been reported to exhibit any gross abnormalities except in the brain (an enhancement in amygdala long-term potentiation), whereas Rabgef1$^{-/-}$ mice exhibit increased perinatal mortality, develop severe inflammation in the skin and exhibit elevated levels of skin mast cells. These findings suggest that the distinct in vivo functional effects exerted by RabGEF1 or RIN1 reflect differences in their ability to interact with cell-specific signaling factors (in addition to Ras and Rab5) to elicit distinct patterns of activation of cell-specific downstream effectors.

In addition to permitting enhanced Ras-dependent signaling and functional responses after challenge with IgE and antigen, a lack of RabGEF1 also resulted in high basal levels of Ras activation and ERK activation in mast cells that were not exposed to antigen challenge. This was more clearly demonstrated in Rabgef1$^{-/-}$ BMCMCs (FIGS. 6b, c) than in CI.MC/C57.1 mast cells that had been transfected with a Rabgef1 antisense expression vector (FIGS. 3b, c). The Rabgef1$^{-/-}$ mast cells, completely lacking RabGEF1, appeared to exhibit a complete loss of its negative regulatory effects on Ras activity. By contrast, the antisense transfectants might well have continued to exhibit some negative regulation of Ras activation as a result of residual RabGEF1 protein expression (FIG. 3a). Moreover, it is possible that some of the differences observed between CI.MC/C57.1 mast cells that had been transfected with a Rabgef1 antisense expression vector and Rabgef1$^{-/-}$ mast cells reflect effects of the lack of RabGEF1 on mast cell development in the Rabgef1$^{-/-}$ mast cells.

The elevated basal levels of Ras and ERK activation observed in Rabgef1$^{-/-}$ BMCMCs may explain, in part, the finding that these cells exhibited enhanced degranulation (as measured by release of β-Hex) in response to FcεRI aggregation. Although early studies suggested that mast cell degranulation and cytokine/lipid mediator release are mediated through two distinct signaling cascades (reviewed in refs. 9-11), recent reports have indicated that these pathways can functionally overlap. Thus, in Rabgef1$^{-/-}$ BMCMCs, the high levels of ERK activation at baseline, and the even higher and more sustained levels of ERK activation after stimulation with IgE and antigen, may promote interactions between the two pathways and thereby lead to enhanced degranulation, as well as enhanced secretion of lipid mediators and cytokines.

Several other molecules that can negatively regulate FcεRI-dependent mast cell activation have been described, but these are distinct from RabGEF1 in both mechanisms of action and patterns of cellular expression. For example, co-aggregation of FcεRI receptors with immunoreceptor tyrosine-based inhibitory motif (ITIM)-containing receptors can initiate inhibitory pathways that can negatively regulate FcεRI-mediated signaling responses in mast cells. Such ITIM-containing receptors, including FcγRIIB (the low affinity IgG receptor), gp49B1, paired Ig-like receptor-B (PIRB) and the mast cell function-associated antigen (MAFA), typically exhibit a restricted cellular distribution, often being expressed mainly in mast cells and other hematopoietic or lymphoid cells. Accordingly, when mice deficient in the expression of such ITIM-containing receptors have been generated, they so far have been healthy and fertile and have exhibited a more restricted set of phenotypic abnormalities than do Rabgef1$^{-/-}$ mice.

By contrast, our studies show that mRNA for Rabgef1 is expressed in many different tissues and cell types, and we find that the targeted mutation of the Rabgef1 gene in mice results in a dramatic phenotype. Many of these knockout pups die within one week of birth, and less than 5% of the pups that can be genotyped are Rabgef1$^{-/-}$ animals. All of the surviving Rabgef1$^{-/-}$ mice eventually develop significant abnormalities in the skin, characterized by epidermal hyperplasia, hyperkeratosis and prominent dermal inflammation. There are increased numbers of mast cells in the skin of Rabgef1$^{-/-}$ mice and mast cell numbers are even higher at sites of significant dermal inflammation. Since high levels of IgE have been shown to enhance mouse mast cell survival in vitro and in vivo, it is possible that the high levels of IgE in the blood of Rabgef1$^{-/-}$ mice may contribute to the high mast cell numbers present in these mice.

Since the development of skin lesions and the increases in numbers of dermal mast cells progress concurrently in Rabgef1$^{-/-}$ mice, mast cells may contribute to the cutaneous inflammation observed in these animals. Indeed, mast cells that exhibit signs of degranulation can be detected in the dermis in histological sections of the skin lesions in Rabgef1$^{-/-}$ mice. Moreover, the high basal levels of activated Ras found in Rabgef1$^{-/-}$ BMCMCs in vitro raises the possibility that high basal levels of Ras activity may also occur in skin mast cells in the Rabgef1$^{-/-}$ mice in vivo. If Rabgef1$^{-/-}$ mice contained mast cells with high basal levels of Ras activity, such cells might be more susceptible than wild-type mast cells to activation by various stimuli present in tissue micro-environments at sites of cutaneous inflammation, leading to the local release of mediators by Rabgef1$^{-/-}$ mast cells in vivo. Indeed, the high levels of histamine detected in the serum of Rabgef1$^{-/-}$ mice are consistent with the possibility that significant degranulation of mast cells does occur in Rabgef1$^{-/-}$ animals even in the absence of challenge with known specific antigen (FIG. 8c).

In conclusion, RabGEF1 can bind physically to Ras and can suppress Ras activation and Ras-mediated functional responses during IgE- and antigen-dependent mast cell activation. Our data provide a model in which changes in levels of RabGEF1 protein can significantly regulate FcεRI-dependent mast cell activation: During the initial phase of mast cell activation, levels of RabGEF1 protein fall, thus facilitating the activation of Ras and its associated downstream pathways; subsequently, as Rabgef1 gene transcription is enhanced and RabGEF1 protein levels are replenished, the higher levels of RabGEF1 protein contribute to the cessation of Ras activation and cellular functional responses in mast cells. However, the importance of RabGEF1 as a negative regulator of Ras-dependent signaling pathways probably extends well beyond mast cell biology. Indeed, the absence of RabGEF1 expression in Rabgef1 knockout mice leads to increased perinatal mortality and the development of severe skin inflammation, as well as increases in numbers of dermal mast cells. While some of the changes affecting the skin in Rabgef1$^{-/-}$ mice may be secondary to the effects of a deficiency of RabGEF1 on mast cell development and/or function, others may reflect disruption of roles of RabGEF1 in keratinocytes, hematopoietic or lymphoid cells, and/or other resident cells besides mast cells. Nevertheless, our data clearly show that RabGEF1 represents an important negative regulator of FcεRI-dependent functional responses in mast cells and that the absence of this protein in vivo results in other striking phenotypic abnormalities as well, including increased perinatal mortality and severe inflammation of the skin.

Methods

Cell culture. Bone marrow-derived cultured mast cells (BMCMCs) were derived from the femoral bone marrow cells of 4-6 week-old BALB/c mice or 3-12 week-old Rabgef1$^{-/-}$ mice or their wild-type littermates. The bone marrow cells were maintained in suspension in IL-3 containing conditioned medium, consisting of complete medium [10% fetal calf serum (FCS) (Sigma) in Dulbecco's Modified Eagle's Medium (GIBCO BRL)] supplemented with 20% (v/v) of either supernatants from Concanavalin A-activated spleen cells or WEHI-3 conditioned medium. After 4-5 weeks, at least 95% of cells that remained in the culture were identifiable as mast cells. CI.MC/C57.1 cells, from a cloned growth factor-independent mouse mast cell line of BALB/c orgin, were maintained in complete medium lacking exogenous growth factors.

Aggregation of high affinity IgE receptors (FcεRI). The IgE and anti-DNP mAb-producing hybridoma H1-DNP-ε26 was used to generate ascites. BMCMCs or CI.MC/C57.1 mast cells were sensitized with the ascites diluted in medium at 8-10 μg/ml for 2 hours or at 2 μg/ml overnight at 37° C., washed with medium, then resuspended with medium containing DNP$_{30-40}$-HSA (Sigma), at various concentrations, at 37° C.

Isolation of mouse Rabgef1 cDNA clone. Differential display was performed using the RNAmap KitA (GenHunter) according to the manufacturer's instructions. A differentially expressed PCR band (designated 60-4) was identified and re-amplified by PCR. The re-amplified PCR segment was subcloned into pGEM-T vector and $^{32}$P-labeled to generate a probe for Northern blot analysis. The radiolabeled 60-4 probe was also used to screen a BMCMC cDNA library constructed in Uni-ZAP XR Vector (Stratagene). One positive clone with a 1.1 kb insert was isolated. To isolate the full-length cDNA, the 1.1 kb cDNA insert was used as a probe to screen a mouse brain cDNA library (Stratagene). A positive clone with a 2.6 kb insert was isolated and sequenced.

Antibodies and Western blot analysis. Anti-actin monoclonal antibody was obtained from Santa Cruz Biotechnology. Anti-p44/42 MAP kinase (ERK) polyclonal antibody and anti-SAPK/JNK polyclonal, antibody were obtained from Cell Signaling Technology. The antibody against the mouse RabGEF1 was generated by immunizing rabbits with a synthetic peptide corresponding to the 16 N-terminal residues of mouse RabGEF1 (KSERRGIHVDQSELLC) (SEQ ID NO: 12) conjugated to keyhole limpet hemacyanin. The antibody was affinity-purified on a peptide column using a cysteine residue of the peptide coupled to an iodoacetamide on Sepharose beads. For Western blotting, cells were lysed in cell lysis buffer (20 mM Tris 7.5, 150 mM NaCl, 1 mM EDTA, 1 mM EGTA, 1% Triton X-100, 2.5 mM sodium pyrophosphate, 1 mM β-glycerolphosphate, 1 mM Na$_3$VO$_4$, 1 μg/ml leupeptin, 1 mM phenyl methylsulfonyl fluoride). Resulting protein lysates were subjected to 10-12% SDS-PAGE and electroblotted onto Immobilon-P membranes (Millipore) or Invitrolon PVDF membranes (Invitrogen). Membranes were blocked in 5% nonfat dry milk in TBS-Tween buffer and then probed with the primary antibody. The antigen-antibody complexes were visualized with horseradish peroxidase-conjugated anti-rabbit or anti-mouse IgG secondary antibody using the Phototope-HRP Weatern Detection Kit (Cell Signaling Technology). The films were scanned and specific signals were quantitated by ImageQuant software (Molecular Dynamics).

Yeast two-hybrid assay. The interactions between mouse RabGEF1 and the mouse or yeast Ras protein were assayed using the MATCHMAKER Two-Hybrid System 2 (Clontech) according to the instructions supplied by the manufacturer. The entire open reading frame and different segments of the open reading frame of the mouse RabGEF1 cDNA were separately subcloned, in frame, into the pACT2 vector. The mouse H-Ras cDNA was generated from total RNA of CI.MC/C57.1 cells by RT-PCR using the 5' primer GCGGMTTCATGAC AGMTACMGCTTGTG (SEQ ID NO: 1) and the 3' primer GACGGATCCCTCAGGACAG-CACACACTTGC (SEQ ID NO: 2) and subcloned into pAS2-1. The yeast Ras2p cDNA was generated from S. cerevisiae poly A+ RNA (Clontech) by RT-PCR using the 5' primer GCGGMTTCATGACAGAATACMGCTTGTG (SEQ ID NO: 3) and the 3' primer GATAGGATCCAC-CCGATCCGCTCTTG (SEQ ID NO: 4) and subcloned into pAS2-1. A Cys-to-Ser mutation at residue 318 of Ras2p, which suppresses palmitolylation, was constructed using the QuikChange Site-Directed Mutagenesis Kit (Stratagene). Y187 yeast strain was cotransformed with the constructs described above and the transformants were selected on—Leu/-Trp plates. β-galactosidase activity was determined for colonies that appeared after 3-4 days using a qualitative colony-lift filter assay with X-gal as substrate and a quantitative liquid culture assay with chlorophenol red-β-D-galactopyranoside as substrate.

Generation of stable Rabgef1 antisense transfectants. The mouse Rabgef1 cDNA clone was digested with XbaI and XhoI, and the entire full-length cDNA insert released was ligated to the pBK-CMV expression vector (Stratagene) to generate the Rabgef1 antisense expression plasmid (Rabgef1-AS). The antisense plasmid and the vector control plasmid (CMV) were transfected separately into C1.MC/C57.1 mast cells using LIPOFECTAMINE Reagent (GIBCO BRL). The transfected cells were selected in Geneticin (G418) (GIBCO BRL) at 2 mg/ml for 10 days and then at 0.8 mg/ml thereafter.

Measurement of mediator release. Levels of $LTC_4$ release were measured using an enzyme immunoassay (EIA) kit (Amersham/Pharmacia), and levels of secretion of TNF-α and IL-6 were assayed using enzyme-linked immunosorbent assay (ELISA) kits (Endogen), according to the manufacturer's instructions. Levels of β-hexosaminidase release were measured on an ELISA reader using p-nitrophenyl-N-acetyl-β-D-glucosamine (Sigma) as previously described. Levels of PGD2 release were measured using an EIA kit (Cayman), according to the manufacturer's instructions.

Measurements of serum levels of IgE and histamine. Levels of serum IgE were determined using an ELISA kit (BD Biosciences/Pharmingen), and levels of serum histamine were determined using an EIA kit (Immunotech), according to the manufacturer's instructions.

Activation of Ras, Rac1, and Cdc42. The activation of Ras activity was assayed using the EZ-Detect Ras Activation Kit (Pierce). Specifically, a GST-fusion protein containing the Ras binding domain (RBD) of Raf-1 was used to pull-down specifically the active GTP-bound Ras. Cell lysate ($10^7$ cells/sample) was incubated with GST-Raf-1-RBD in the presence of a SwellGel Immobilized Glutathione Disc (Pierce) at 4° C. for 2-3 hours and the pulled-down Ras-GTP was detected by Western blot analysis using an anti-pan-isoform specific Ras antibody. The activation of Rac1 and Cdc42 was assayed using the EZ-Detect Rac1 Activation Kit (Pierce) and the EZ-Detect Cdc42 Activation Kit (Pierce), respectively. Specifically, a GST-fusion protein containing the p21-binding domain (PBD) of human Pak1 was used to pull-down specifically the active GTP-bound Rac1 or Cdc42. The GST-Pak1-PBD fusion protein was incubated with cell lysate in the presence of a SwellGel Immobilized Glutathione Disc. The pulled-down active Rac1 or Cdc42 was detected by Western blot analysis using an anti-Rac1 antibody or anti-Cdc42 antibody, respectively.

ERK and JNK activation. ERK activity was assayed using the p44/42 MAP Kinase Assay Kit (Cell Signaling Technology). Specifically, an immobilized phospho-p44/42 MAP kinase (Thr202/Tyr204) monoclonal antibody was used to immunoprecipitate the active p44/42 ERK from cell lysates ($10^7$ cells/sample). Immunoprecipitates were incubated in the presence of 100 mM ATP and 1 μg of Elk-1 fusion protein substrate for 30 minutes at 30° C. The phosphorylation of Elk-1 protein by p44/42 ERK was detected by Western blot analysis using an anti-phospho-Elk-1 (Ser383) antibody. JNK activity was assayed using the SAPK/JNK Assay Kit (Cell Signaling Technology). Specifically, c-Jun (1-89) GST-fusion protein was used to immunoprecipitate JNK. The phosphorylation of the c-Jun fusion protein by JNK at Ser63 was detected by Western blot analysis using an anti-phospho-c-Jun (Ser63) antibody.

Generation of Rabgef1$^{-/-}$ mice. Genomic clones spanning the Rabgef1 locus were isolated from a 129/SvJ FIX II λ phage genomic library (Stratagene) using the full-length Rabgef1 cDNA as a probe and subcloned into pBluescript (Stratagene). A 1.7 kb StuI fragment containing part of exon 3 was cloned 5' of the 3' end of the neomycin gene in the pLNLvector. A second 7.2 kb fragment extending from the KpnI site 3' of exon 3 to the NheI site in intron 4 was cloned 5' to the neomycin gene. The targeting construct plasmid was linearized and electroporated into E14TG2a ES cells, and transformed cells were selected in G418. Targeted clones were identified by Southern blot analysis and microinjected into C57BL/6 blastocysts to generate chimeras, which were bred to C57BL/6 or 129/SvEv mice to generate the heterozygous Rabgef1$^±$ mice. Rabgef1$^{-/-}$ mice and their wild-type littermates were subsequently generated from the intercross of the heterozygous animals.

Flow cytometry. BMCMCs derived from the Rabgef1$^{-/-}$, Rabgef1$^±$, and wild-type mice were washed with PBS, resuspended in PBS containing 2% FCS, and incubated for 15 minutes with monoclonal antibodies against CD 16/32 (Clone 2.4G2; BD Biosciences/Pharmingen) and CD23 (Clone B3B4; BD Biosciences/Pharmingen) to block non-specific binding. Cells were then incubated with mouse IgE (Sigma) for 45 minutes and stained for 30 minutes with APC-anti-c-kit monoclonal antibody (Clone 2B8; BD Biosciences/Pharmingen) and FITC-anti-IgE monoclonal antibody (Clone R35-72; BD Biosciences/Pharmingen). Stained cells were analyzed for FcεRI expression using a FACS-Vantage flow cytometer (Becton Dickinson). Dead cells were excluded by propidium iodide gating and data were analyzed with FlowJo software (Treestar).

GenBank accession number. Mouse RabGEF 1 (Rabex-5/Rin2) mRNA, AF093590

What is claimed is:

1. A transgenic mouse model for RabGEF1 function comprising in its genome a homozygous disruption of the rabgef1 gene that results in no expression of RabGEF1, wherein the mouse has a phenotype of skin inflammation.

2. A method of screening a biologically active agent for treatment of skin inflammation comprising administering a biologically active agent to the transgenic mouse model of claim 1 and determining the effect of said agent on the skin inflammation of said transgenic mouse model, wherein a reduction of the skin inflammation identifies a biologically active agent for the treatment of skin inflammation.

* * * * *

SEQUENCE LISTING

<160> NUMBER OF SEQ ID NOS: 12

<210> SEQ ID NO 1
<211> LENGTH: 30
<212> TYPE: DNA
<213> ORGANISM: Artificial Sequence
<220> FEATURE:
<223> OTHER INFORMATION: synthetic primer

<400> SEQUENCE: 1
gcggaattca tgacagaata caagcttgtg                                    30

<210> SEQ ID NO 2
<211> LENGTH: 30
<212> TYPE: DNA

```
-continued

<213> ORGANISM: Artificial Sequence
<220> FEATURE:
<223> OTHER INFORMATION: synthetic primer

<400> SEQUENCE: 2
gacggatccc tcaggacagc acacacttgc                                       30

<210> SEQ ID NO 3
<211> LENGTH: 30
<212> TYPE: DNA
<213> ORGANISM: Artificial Sequence
<220> FEATURE:
<223> OTHER INFORMATION: synthetic primer

<400> SEQUENCE: 3
gcggaattca tgacagaata caagcttgtg                                       30

<210> SEQ ID NO 4
<211> LENGTH: 26
<212> TYPE: DNA
<213> ORGANISM: Artificial Sequence
<220> FEATURE:
<223> OTHER INFORMATION: synthetic primer

<400> SEQUENCE: 4
gataggatcc acccgatccg ctcttg                                           26

<210> SEQ ID NO 5
<211> LENGTH: 148
<212> TYPE: PRT
<213> ORGANISM: mouse

<400> SEQUENCE: 5
```

Glu Thr Thr Asp Asp Glu Lys Lys Asp Leu Ala Ile Gln Lys Arg Ile
 1               5                  10                  15

Arg Ala Leu His Trp Val Thr Pro Gln Met Leu Cys Val Pro Val Asn
            20                  25                  30

Glu Glu Ile Pro Glu Val Ser Asp Met Val Val Lys Ala Ile Thr Asp
        35                  40                  45

Ile Ile Glu Met Asp Ser Lys Arg Val Pro Arg Asp Lys Leu Ala Cys
    50                  55                  60

Ile Thr Arg Cys Ser Lys His Ile Phe Asn Ala Ile Lys Ile Thr Lys
65                  70                  75                  80

Asn Glu Pro Ala Ser Ala Asp Asp Phe Leu Pro Thr Leu Ile Tyr Ile
                85                  90                  95

Val Leu Lys Gly Asn Pro Pro Arg Leu Gln Ser Asn Ile Gln Tyr Ile
            100                 105                 110

Thr Arg Phe Cys Asn Pro Ser Arg Leu Met Thr Gly Glu Asp Gly Tyr
        115                 120                 125

Tyr Phe Thr Asn Leu Cys Cys Ala Val Ala Phe Ile Glu Lys Leu Asp
    130                 135                 140

Ala Gln Ser Leu
145

```
<210> SEQ ID NO 6
<211> LENGTH: 147
<212> TYPE: PRT
<213> ORGANISM: yeast

<400> SEQUENCE: 6
```

Glu His Met Lys Asp Leu Thr Asn Asp Asp Thr Leu Leu Glu Lys Ile

```
            1               5                  10                 15
Arg His Tyr Arg Phe Ile Ser Pro Ile Met Leu Asp Ile Pro Asp Thr
                20                 25                 30

Met Pro Asn Ala Arg Leu Asn Lys Phe Val His Leu Ala Ser Lys Glu
                35                 40                 45

Leu Gly Lys Ile Asn Arg Phe Lys Ser Pro Arg Asp Lys Met Val Cys
                50                 55                 60

Val Leu Asn Ala Ser Lys Val Ile Phe Gly Leu Lys His Thr Lys
 65                 70                 75                 80

Leu Glu Gln Asn Gly Ala Asp Ser Phe Ile Pro Val Leu Ile Tyr Cys
                85                 90                 95

Ile Leu Lys Gly Gln Val Arg Tyr Leu Val Ser Asn Val Asn Tyr Ile
               100                105                110

Glu Arg Phe Arg Ser Pro Asp Phe Ile Arg Gly Glu Glu Tyr Tyr
               115                120                125

Leu Ser Ser Leu Gln Ala Ala Leu Asn Phe Ile Met Ser Leu Thr Glu
               130                135                140

Arg Ser Leu
145

<210> SEQ ID NO 7
<211> LENGTH: 143
<212> TYPE: PRT
<213> ORGANISM: Homo sapien

<400> SEQUENCE: 7

Arg Leu Ala Ala Asp Gly Ser Leu Gly Arg Leu Ala Glu Gly Leu Arg
 1               5                  10                 15

Leu Ala Arg Ala Gln Gly Pro Gly Ala Phe Gly Ser His Leu Ser Leu
                20                 25                 30

Pro Ser Pro Val Glu Leu Glu Gln Val Arg Gln Lys Leu Leu Gln Leu
                35                 40                 45

Val Arg Thr Tyr Ser Pro Ser Ala Gln Val Lys Arg Leu Leu Gln Ala
                50                 55                 60

Cys Lys Leu Leu Tyr Met Ala Leu Arg Thr Gln Glu Gly Glu Gly Ser
 65                 70                 75                 80

Gly Ala Asp Gly Phe Leu Pro Leu Leu Ser Leu Val Leu Ala His Cys
                85                 90                 95

Asp Leu Pro Glu Leu Leu Leu Glu Ala Glu Tyr Met Ser Glu Leu Leu
               100                105                110

Glu Pro Ser Leu Leu Thr Gly Glu Gly Gly Tyr Tyr Leu Thr Ser Leu
               115                120                125

Ser Ala Ser Leu Ala Leu Leu Ser Gly Leu Gly Gln Ala His Thr
               130                135                140

<210> SEQ ID NO 8
<211> LENGTH: 143
<212> TYPE: PRT
<213> ORGANISM: Homo sapien

<400> SEQUENCE: 8

Phe His Met Ala Asp Gly Ser Trp Lys Gln Leu Lys Glu Asn Leu Gln
 1               5                  10                 15

Leu Val Arg Gln Arg Asn Pro Gln Glu Leu Gly Val Phe Ala Pro Thr
                20                 25                 30

Pro Asp Phe Val Asp Val Glu Lys Ile Lys Val Lys Phe Met Thr Met
```

-continued

```
                   35                  40                  45
Gln Lys Met Tyr Ser Pro Glu Lys Lys Val Met Leu Leu Arg Val
    50                  55                  60

Cys Lys Leu Ile Tyr Thr Val Met Glu Asn Asn Ser Gly Arg Met Tyr
65                  70                  75                  80

Gly Ala Asp Asp Phe Leu Pro Val Leu Thr Tyr Val Ile Ala Gln Cys
                85                  90                  95

Asp Met Leu Glu Leu Asp Thr Glu Ile Glu Tyr Met Met Glu Leu Leu
                100                 105                 110

Asp Pro Ser Leu Leu His Gly Gly Gly Tyr Tyr Leu Thr Ser Ala
            115                 120                 125

Tyr Gly Ala Leu Ser Leu Ile Lys Asn Phe Gln Glu Glu Gln Ala
    130                 135                 140

<210> SEQ ID NO 9
<211> LENGTH: 9
<212> TYPE: PRT
<213> ORGANISM: Artificial Sequence
<220> FEATURE:
<223> OTHER INFORMATION: synthetic motif
<220> FEATURE:
<221> NAME/KEY: VARIANT
<222> LOCATION: 3, 4
<223> OTHER INFORMATION: Xaa = Any Amino Acid

<400> SEQUENCE: 9

Leu Leu Xaa Xaa Cys Lys Leu Ile Tyr
1               5

<210> SEQ ID NO 10
<211> LENGTH: 9
<212> TYPE: PRT
<213> ORGANISM: Artificial Sequence
<220> FEATURE:
<223> OTHER INFORMATION: synthetic motif
<220> FEATURE:
<221> NAME/KEY: VARIANT
<222> LOCATION: 4
<223> OTHER INFORMATION: Xaa = Any Amino Acid

<400> SEQUENCE: 10

Gly Ala Asp Xaa Phe Leu Pro Val Leu
1               5

<210> SEQ ID NO 11
<211> LENGTH: 9
<212> TYPE: PRT
<213> ORGANISM: Artificial Sequence
<220> FEATURE:
<223> OTHER INFORMATION: synthetic motif
<220> FEATURE:
<221> NAME/KEY: VARIANT
<222> LOCATION: 3, 4
<223> OTHER INFORMATION: Xaa = Any Amino Acid

<400> SEQUENCE: 11

Gly Glu Xaa Xaa Tyr Tyr Leu Thr Ser
1               5

<210> SEQ ID NO 12
<211> LENGTH: 16
<212> TYPE: PRT
<213> ORGANISM: mouse
```

-continued

```
<400> SEQUENCE: 12

Lys Ser Glu Arg Arg Gly Ile His Val Asp Gln Ser Glu Leu Leu Cys
1               5                   10                  15
```